(12) United States Patent
Lu et al.

(10) Patent No.: US 10,472,326 B2
(45) Date of Patent: Nov. 12, 2019

(54) PQSR MODULATORS

(71) Applicant: HELMHOLTZ-ZENTRUM FÜR INFEKTIONSFORSCHUNG GMBH, Braunschweig (DE)

(72) Inventors: Cenbin Lu, Saarbrücken (DE); Christine K. Maurer, Homburg (DE); Benjamin Kirsch, Saarbrücken (DE); Anke Steinbach, St. Ingbert (DE); Rolf W. Hartmann, Saarbrücken (DE); Mathias Müsken, Braunschweig (DE); Susanne Häussler, Salzgitter (DE)

(73) Assignee: HELMHOLTZ-ZENTRUM FÜR INFEKTIONSFORSCHUNG GMBH, Braunschweig (DE)

( * ) Notice: Subject to any disclaimer, the term of this patent is extended or adjusted under 35 U.S.C. 154(b) by 0 days.

(21) Appl. No.: 15/301,192

(22) PCT Filed: Apr. 3, 2014

(86) PCT No.: PCT/EP2014/000893
§ 371 (c)(1),
(2) Date: Sep. 30, 2016

(87) PCT Pub. No.: WO2015/149821
PCT Pub. Date: Oct. 8, 2015

(65) Prior Publication Data
US 2017/0022165 A1    Jan. 26, 2017

(51) Int. Cl.
| C07D 215/233 | (2006.01) |
| C07D 215/38 | (2006.01) |
| C07D 215/56 | (2006.01) |
| C07D 471/04 | (2006.01) |
| A61K 31/47 | (2006.01) |
| A61K 45/06 | (2006.01) |
| A61L 31/16 | (2006.01) |
| C07D 215/48 | (2006.01) |

(52) U.S. Cl.
CPC .......... *C07D 215/233* (2013.01); *A61K 31/47* (2013.01); *A61K 45/06* (2013.01); *A61L 31/16* (2013.01); *C07D 215/38* (2013.01); *C07D 215/48* (2013.01); *C07D 215/56* (2013.01); *C07D 471/04* (2013.01); *A61L 2300/404* (2013.01); *A61L 2300/606* (2013.01)

(58) Field of Classification Search
CPC .............. C07D 215/233; C07D 215/38; C07D 215/48; C07D 215/56; C07D 471/04; A61K 31/47; A61K 45/06
USPC ........................................................ 514/312
See application file for complete search history.

(56) References Cited

U.S. PATENT DOCUMENTS 7,482,362 B2 * 1/2009 Pritchard ............... A61K 31/47
514/311

FOREIGN PATENT DOCUMENTS

WO    WO00/08026    * 2/2000    ........... C07D 491/00

OTHER PUBLICATIONS

McGlacken et al. Tetrahedron Letters, 2010, 51, 5919-5921.*
McGlarken et al. Tetrahedron Letters, 2010, 51, 5919-5921.*
Kay et al (Journal of the Chemical Society, section C, 1968, pp. 2656-2661 (Year: 1968).*
Ilangovan et al., PLOS pathogens, 2013, 9(7), e1003508 (Year: 2013).*
Rahal Clinical Infectious Diseases, 2006, 43, S95-9 (Year: 2006).*
Frei et al., "Aminobenzimidazole Derivatives Strongly Inhibit and Disperse Pseudomonas aeruginosa Biofilms". Angewandte Chemie International Edition English, May 21, 2012, vol. 51(21), pp. 5226-5229.
Yang et al., "Computer-Aided Identification of Recognized Drugs as Pseudomonas aeruginosa Quorum-Sensing Inhibitors", Antimicrobial Agents and Chemotherapy, Jun. 2009, pp. 2432-2443.
O'Louglin et al., "A Quorum-Sensing Inhibitor Blocks Pseudomonas aeruginosa Virulence and Biofilm Formation", Proceedings of the National Academy of Sciences, Oct. 29, 2013, vol. 110, No. 44, pp. 17981-17986.
Hentzer et al., "Attenuation of Pseudomonas aeruginosa Virulence by Quorum Sensing Inhibitors", The EMBO Journal, vol. 22, No. 15, 2003, pp. 3803-3815.
Hentzer et al., "Inhibition of Quorum Sensing in Pseudomonas aeruginosa Biofilm Bacteria by a Halogenated Furanone Compound", Microbiology, 2002, vol. 148, pp. 87-102.
Rasmussen et al., "Identity and Effects of Quorum-Sensing Inhibitors Produced by Penicillium Species", Microbiology 2005, vol. 151, pp. 1325-1340.
Jakobsen et al., "Ajoene, a Sulfur-Rich Molecule from Garlic, Inhibits Genes Controlled by Quorum Sensing", Antimicrobial Agents and Chemotherapy, May 2012, vol. 56, No. 5, pp. 2314-2325.
Hinsberger et al., "Benzamidobenzoic Acids as Potent PqsD Inhibitors for the Treatment of Pseudomonas aeruginosa infections", European Journal of Medicinal Chemistry, 2014, vol. 76, pp. 343-351.
Storz et al., "Biochemical and Biophysical Analysis of a Chiral PqsD Inhibitor Revealing Tight-binding Behavior and Enantiomers with Contrary Thermodynamic Signatures", American Chemical Society Chemical Biology, 2013, vol. 8, pp. 2794-2801.
Sahner et al., "Combining in Silico and Biophysical Methods for the Development of Pseudomonas aeruginosa Quorum Sensing Inhibitors: An Alternative Approach for Structure-Based Drug Design", Journal of Medicinal Chemistry, 2013, vol. 56, pp. 8656-8664.
Weidel et al., "Structure Optimizer of 2-Benzamidobenzoic Acids as PqsD Inhibitors for Pseudomonas aeruginosa Infections and Elucidation of Binding Mode by SPR, STD NMR, and Molecular Docking", Journal of Medicinal Chemistry, 2013, vol. 56, pp. 6146-6155.

(Continued)

*Primary Examiner* — Yevgeny Valenrod
(74) *Attorney, Agent, or Firm* — Mintz Levin Cohn Ferris Glovsky and Popeo, P.C.; Peter F. Corless

(57) ABSTRACT

The present invention relates to compounds according to general formula (I); to pharmaceutical compositions comprising one or more of the compound(s); and to the use of the compound(s) as anti-infectives.

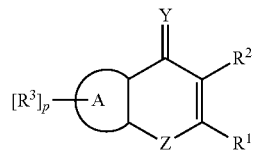

9 Claims, 1 Drawing Sheet

(56) References Cited

OTHER PUBLICATIONS

Calfee et al., "Interference with Pseudomonas quinolone signal synthesis inhibits virulence factor expression by Pseudomonas aeruginosa", Proceedings of the National Academy of Sciences, Sep. 25, 2001, vol. 98, No. 20, pp. 11633-11637.
Pistorius et al., "Biosynthesis of 2-Alkyl-4 (1H)-Quinolones in Pseudomonas aeruginosa: Potential for Therapeutic Interference with Pathogenicity", ChemBioChem, 2011, vol. 12, pp. 850-853.
Pistorius et al., "Biosynthesis of 2-Alkyl-4 (1H)-Quinolones in Pseudomonas aeruginosa: Potential for Therapeutic Interference with Pathogenicity"—Supporting Information, ChemBioChem, 2011, pp. 1-13.
Lesic et al., "Inhibitors of Pathogen Intercellular Signals as Selective Anti-Infective Compounds". PLoS Pathogens, Sep. 2007, vol. 3, Issue 9, pp. 1229-1239.
Storz et al., "Validation of PqsD as an Anti-biofilm Targed in Pseudomonas aeruginosa by Development of Small-Molecule Inhibitors", Journal of the American Chemical Society, 2012, vol. 134, pp. 16143-16146.
Coleman et al., "Pseudomonas aeruginosa PqsA Is an Anthranilate-Coenzyme A Ligase", American Society for Microbiology, 2008, vol. 190, No. 4, pp. 1247-1255.
Klein et al., "Identification of Small-Molecule Antagonists of the Pseudomonas aeruginosa Transcriptional Regulator PqsR: Biophysically Guided Hit Discovery and Optimization", American Chemical Society Chemical Biology, 2012, vol. 7, pp. 1496-1501.
Zender et al., "Discovery and Biophysical Characterization of 2-Amino-oxadiazoles as Novel Antagonists of PqsR, an Important Regulator of Pseudomonas aeruginosa Virulence", Journal of Medicinal Chemistry, 2013, vol. 56, pp. 6761-6774.
Lu et al., "Discovery of Antagonists of PqsR, a Key Player in 2-Alkyl-4-quinolone-Dependent Quorum Sensing in Pseudomonas aeruginosa" Chemistry & Biology, Mar. 23, 2012, vol. 19, pp. 381-390.
Lu et al., "Overcoming the Unexpected Functional Inversion of a PqsR Antagonist in Pseudomonas aeruginosa: An In Vivo Potent Antivirulence Agent Targeting pqs Quorum Sensing", Angewandte Chemie International Edition, 2014, vol. 53, pp. 1109-1112.
Ilangovan et al., "Structural Basis for Native Agonist and Synthetic Inhibitor Recognition by the Pseudomonas aeruginosa Quorum Sensing Regulator PqsR (MvfR)", PLOS Pathogens, Jul. 2013, vol. 9, No. 7, pp. 1-17.
Maurer et al., "Development and validation of a UHPLC-MS/MS procedure for quantification of the Pseudomonas Quinolone Signal in bacterial culture after acetylation for characterization of new quorum sensing inhibitors", Journal of Pharmaceutical and Biomedical Analysis, 2013, vol. 86, pp. 127-134.
Zhang et al., Enhanced Octadecane Dispersion and Biodegradation by a Pseudomonas Rhamnolipid Surfactant (Biosurfactant), Applied and Environmental Microbiology, Oct. 1992, vol. 58, No. 10, pp. 3276-3282.
Essar, et al., "Identification and Characterization of Genes for a Second Anthranilate Synthase in Pseudomonas aeruginosa: Interchangeability of the Two Anthranilate Synthases and Evolutionary implications", Journal of Bacteriology, Feb. 1990, vol. 172, No. 2, pp. 884-900.
Musken et al., "Genetic determinants of Pseudomonas aeruginosa biofilm establishment", Microbiology, 2010, vol. 156, pp. 431-441.
Musken et al., "A 96-well-plate-based optical method for the quantitative and qualitative evaluation of Pseudomonas aeruginosa biofilm formation and its application to susceptibility testing", Nature Protocols, 2010, vol. 5, No. 8, pp. 1460-1469.
Lu et al., Overcoming the Uexpected Functional Inversion of a PqsR Antagonist in Pseudomonas aeruginosa: An In Vivo Potent Antivirulence Agent Targeting pqs Quorum Sensing, Supporting Information, Angewandte Chemie, Int. Ed. 2014, vol. 53, pp. 1109-1112.

\* cited by examiner

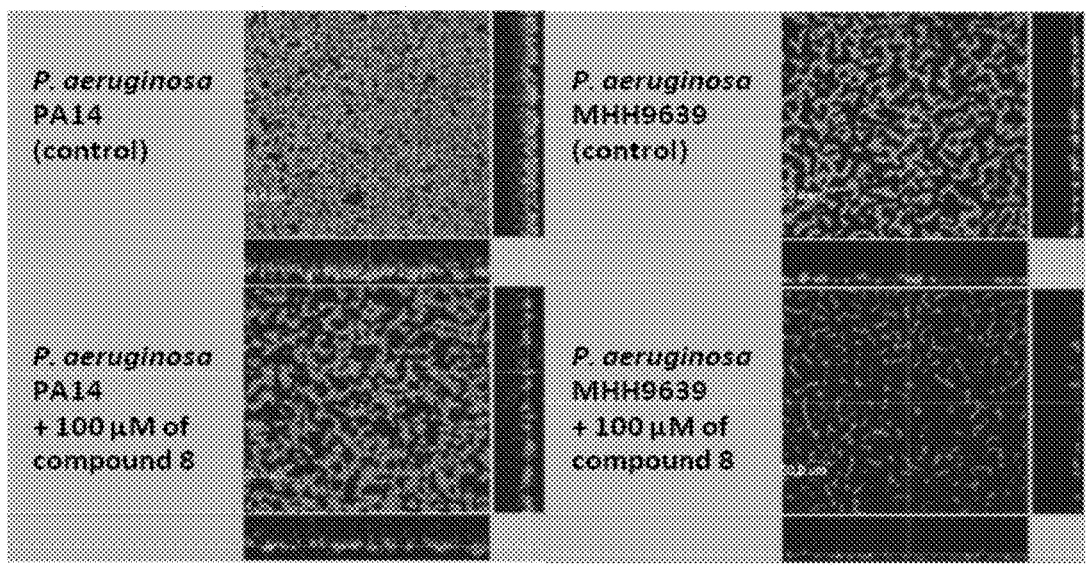

PQSR MODULATORS

This application is a national Phase application filed under 35 U.S.C. § 371 of PCT International Application No. PCT/EP2014/000893 with an International Filing Date of Apr. 3, 2014, the entire contents of which are incorporated herein by reference.

FIELD OF THE INVENTION

The present invention relates to compounds according to general formula (I); to pharmaceutical compositions comprising one or more of the compound(s); and to the use of the compound(s) as anti-infectives.

BACKGROUND OF THE INVENTION

In view of the rapid decline in the effectiveness of antibiotics due to the emergence of resistance, there is a need for a constant supply of new compounds for effective treatment of infections. The development of antimicrobial resistance is mainly attributed to the overuse of antibiotics interfering with essential metabolic processes in bacteria. Moreover, bacteria living in biofilms, sessile cell communities embedded in a matrix of extracellular polymeric substances showing reduced metabolic activity and growth rate, exhibit up to 1000 fold higher resistance against antibiotics than free-living bacteria. Thus, novel therapeutic approaches that aim at reducing bacterial pathogenicity by interfering with bacterial virulence and biofilm formation instead of their metabolic activity are considered as highly favourable and are urgently needed.

The opportunistic pathogen *Pseudomonas aeruginosa* causes severe and fatal infections including such of the urinary tract, of the gastrointestinal tract, of chronic and burnt wounds, of the eyes, of the ears, and of the lungs. Its pathogenicity is strongly related to the expression of virulence factors causing progressive tissue damage and biofilm formation hindering a successful drug therapy. The regulation of pathogenicity is based on a cell-density dependent intercellular communication system known as quorum sensing (QS).

*P. aeruginosa* uses as signal molecules N-acyl-L-homoserine lactones (AHLs) for the las and rhl QS systems and 2-alkyl-4-(1H)-quinolones (AQs) for the pqs QS system. The latter is restricted to *Pseudomonas* and *Burkholderia* species allowing for selective therapy with pqs QS inhibitors. While *Pseudomonas* and *Burkholderia* both produce 2-heptyl-4-hydroxyquinoline (HHQ), *Pseudomonas* uniquely uses the *Pseudomonas* quinolone signal (PQS) as signal molecule. PQS and its biosynthetic precursor HHQ serve as the natural ligands and agonists of the key DNA-binding receptor PqsR. This transcriptional regulator fine-tunes a large set of genes, notably such involved in the biosynthesis of HHQ and in the production of virulence factors such as pyocyanin and lectins. Regarding biofilms, the production of extracellular DNA (eDNA) and lectins, both main biofilm matrix components, is controlled by the pqs QS system. A pqsR mutant of *P. aeruginosa* is pqs QS-deficient, does not produce any pyocyanin or lectin A, shows reduced eDNA production, and displays reduced pathogenicity in mice.

To date, a number of compounds have been discovered that target QS in *Pseudomonas aeruginosa*. The majority of these compounds has been reported to interfere with the AHL-based QS systems in *Pseudomonas* either via direct interaction with the receptors LasR [1, 2] or RhlR [3], at the posttranscriptional level [4-6], or at superior regulatory systems [7]. However, except an extract from *Allium sativum* (garlic), that exhibited no significant improvement of lung function in a clinical trial, these QS inhibitors have been only used in preclinical studies. Whereas AHL-mediated QS is widespread among Gram-negative bacteria, interference with pqs QS allows for selective therapy avoiding adverse effects on beneficial bacterial consortia present in the host. A few pqs QS inhibitors have been described acting as blockers of the signal molecule biosynthesis [8-16] or as antagonists of the receptor PqsR [17-21] A QS inhibitor based on anthranilate structure, methyl anthranilate, was shown to inhibit PQS formation and the production of the virulence factor elastase at millimolar concentrations [12]. QS inhibitors targeting the enzyme PqsA were able to reduce the production of signal molecules HHQ and PQS ($IC_{50}$: ~100 µM for 6FABA) [14, 16, 22] and enhanced the survival rate of *Pseudomonas*-infected mice in a thermal injury mice model [14]. However, high concentrations were necessary to obtain an in cellulo or in vivo effect. Inhibitors of the enzyme PqsD were able to reduce the biovolume of a *P. aeruginosa* biofilm [15], however, did not exhibit any anti-virulence properties (no effect on virulence factor pyocyanin, no effect on the survival of *Pseudomonas*-infected *Galleria mellonella* larvae; unpublished data). Zender [18] and Klein [17] reported PqsR antagonists affecting the production of virulence factor pyocyanin, however with moderate potency ($IC_{50}$ values in the double-digit micromolar range). Furthermore, these compounds did not inhibit biofilm formation (unpublished data). Quinazoline-based PqsR antagonists developed in the group of Paul Williams [21] were reported to exhibit anti-virulence activity. However, the most promising compound was only moderately active in reducing pyocyanin production ($IC_{50}$~50 µM in a less PQS- and pyocyanin-producing *P. aeruginosa* strain). A reduction in biomass of a *P. aeruginosa* biofilm by this compound was observed, however at an unknown concentration. The most potent antagonist of PqsR to date—2-heptyl-6-nitro-4-oxo-1,4-dihydroquinoline-3-carboxamide—was developed in the group of Anke Steinbach and Rolf W. Hartmann [20]. 2-heptyl-6-nitro-4-oxo-1,4-dihydroquinoline-3-carboxamide is highly affine to PqsR ($IC_{50}$=35 nM in *E. coli* reporter gene assay, $IC_{50}$=400 nM in *P. aeruginosa* reporter gene assay), strongly reduces signal molecule production (HHQ production by 54% and PQS by 37% at 15 µM), and shows excellent anti-virulence potency in cellulo (inhibition of virulence factor pyocyanin production: $IC_{50}$=2 µM) and in in vivo animal infection models (strong protection of *Caenorhabditis elegans* nematodes and full protection of *Galleria mellonella* larvae from lethal *P. aeruginosa* infection at a concentration of 22 nM corresponding to 7.3 ng $g^{-1}$ body weight). Most notably, the compound exhibited no sign of toxicity in the two animal models. However, this compound has the disadvantage of not being able to inhibit biofilm formation.

Therefore, the problem underlying the present invention is to provide novel anti-pathogenic compounds exhibiting both anti-virulence and anti-biofilm activity, especially compounds having PqsR modulating, e.g. antagonistic activity to thereby permit an effective treatment of bacterial infections.

SUMMARY AND DESCRIPTION OF THE INVENTION

The present invention relates to a compound of the general formula (I):

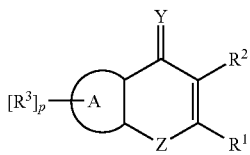

or a pharmacologically acceptable salt thereof, wherein

A represents a fused 5- or 6-membered saturated, unsaturated or aromatic carbocyclic or heterocyclic ring;

$R^1$ is $E-R^{11}$;

E represents a $C_{4-9}$ alkylene, $C_{4-9}$ alkenylene, or $C_{4-9}$ alkynylene group, in which 1 to 5 H atoms may, independently of each other, be replaced by a halogen atom; and/or one or two non-adjacent $CH_2$ groups in L may be replaced by O, NH, or S;

$R^1$ is $CH_{1-3}$, $CHX$, $CH_2X$, $CHX_2$, $CX_3$, CN, $OR^4$, $NR^5R^6$, a phenyl, pyridinyl or morpholino group;

$R^2$ represents a halogen atom, CN, $CF_3$, $NO_2$, $NH_2$, —$NHC(=O)R^4$, —$NHSO_2R^4$, $OR^4$, $(CH_2)_mOR^4$, $SOCH_3$, SOCN, $SOCF_3$, $SO_2CH_3$, $SO_2CN$, $SO_2CF_3$, $SO_2NR^5R^6$, $CO_2H$, $C(=O)OC_{1-6}$ alkyl, $C(=O)NHOR^4$, $COCH_3$, $COCF_3$, $C(CN)_3$; or a $C_{1-6}$ alkyl, $C_{2-6}$ alkenyl, or $C_{2-6}$alkynyl group, in which 1 to 5 H atoms may, independently of each other, be replaced by halogen atom, CN, $CF_3$, $NO_2$, $NH_2$, —$NHC(=O)R^4$, —$NHSO_2R^4$, $(CH_2)_mOR^4$, $SOCH_3$, SOCN, $SOCF_3$, $SO_2CH_3$, $SO_2CN$, $SO_2CF_3$, $SO_2NR^5R^6$, $CO_2H$, $C(=O)OC_{1-6}$ alkyl, $C(=O)NR^5R^6$, $COCH_3$, $COCF_3$, $C(CN)_3$, and/or in which one or two non-adjacent $CH_2$ groups may be replaced by O or NH;

$R^3$ in each case, independently of one another, represents H, halogen atom, CN, $CF_3$, $NO_2$, $NH_2$, —$NHC(=O)R^4$, —$NHSO_2R^4$, $(CH_2)_mOR^4$, $SOCH_3$, SOCN, $SOCF_3$, $SO_2CH_3$, $SO_2CN$, $SO_2CF_3$, $SO_2NR^5R^6$, $C(=O)OC_{1-6}$ alkyl, $C(=O)NR^5R^6$, $COCH_3$, $COCF_3$, or $C(CN)_3$;

$R^4$ in each case, independently of one another, represents a hydrogen atom; an alkyl; alkenyl; alkynyl; heteroalkyl; cycloalkyl; heterocycloalkyl; aryl; heteroaryl; aralkyl; or heteroaralkyl group;

$R^5$ and $R^6$ each independently represents a hydrogen atom; a methyl, an ethyl or an isopropyl group; or $R^5$ and $R^6$ are taken together to form a 5- to 8-membered saturated, unsaturated or aromatic heterocycle containing 1 to 4 N atoms or 1 to 3 heteroatoms selected from the group consisting of nitrogen, oxygen and sulphur, which heterocycle may be unsubstituted or mono-, di or trisubstituted by a halogen atom or R; or $R^5$ and $R^6$ are taken together to form a 5- to 8-membered saturated, unsaturated or aromatic heterocycle containing 1 to 3 heteroatoms selected from the group consisting of nitrogen, oxygen and sulphur, which is fused to one or two rings selected from the group consisting of cycloalkyl; heterocycloalkyl; alkylcycloalkyl; heteroalkylcycloalkyl; aryl; heteroaryl; aralkyl; and heteroaralkyl;

R represents H; —$(CH_2)_p$-L; —$(CH_2)_p$—OL; a $C_{1-6}$ heteroalkyl; a cycloalkyl; a heterocycloalkyl; an alkylcycloalkyl; a heteroalkylcycloalkyl; an aryl; a heteroaryl; an aralkyl; or a heteroaralkyl group;

L represents a $C_{1-6}$ alkyl, $C_{2-6}$ alkenyl, or $C_{2-6}$ alkynyl group, in which 1 to 5 H atoms may, independently of each other, be replaced by halogen atom, CN, $CF_3$, $NO_2$, OR or NHR, and/or in which one or two non-adjacent $CH_2$ groups may be replaced by O, NH, S, SO, or $SO_2$, or $C_{3-7}$ cycloalkyl;

Y represents O, S, NH, or N—$C_{1-6}$ alkyl;

Z represents O, NH, NOH, N—$C_{1-6}$ alkyl; or a single or double bond;

m represents an integer from 1 to 6; and p represents 0, 1, or 2, wherein the following compounds are excluded:

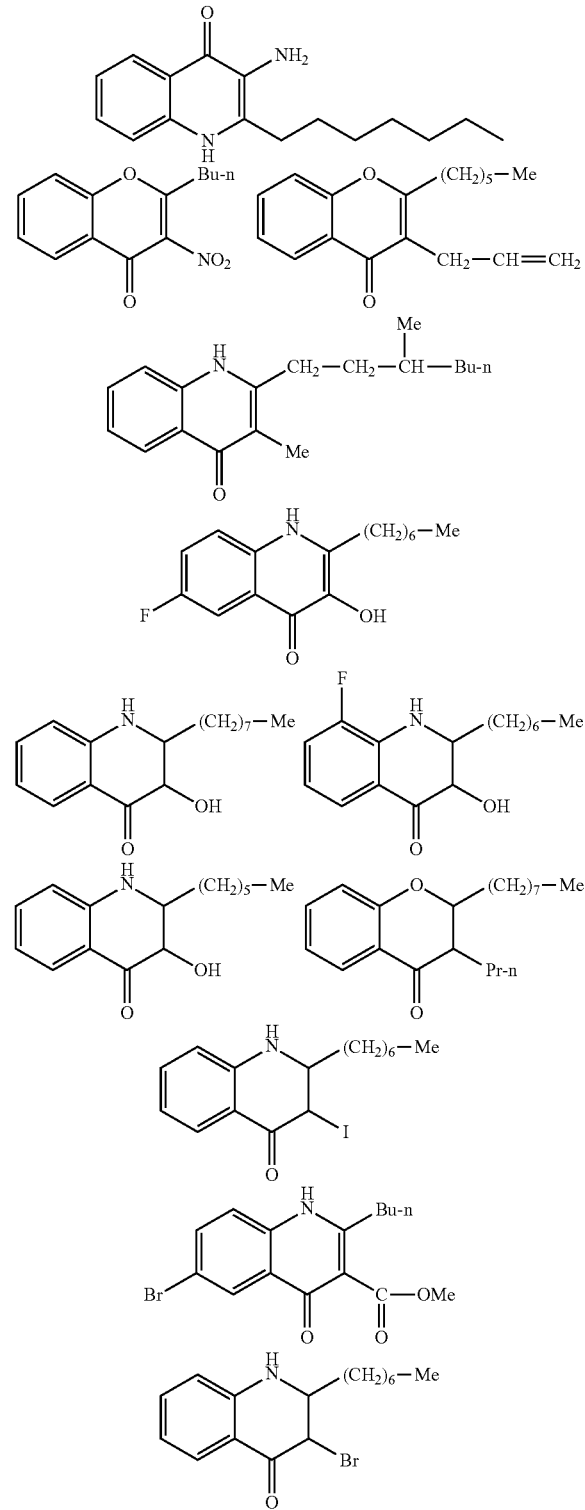

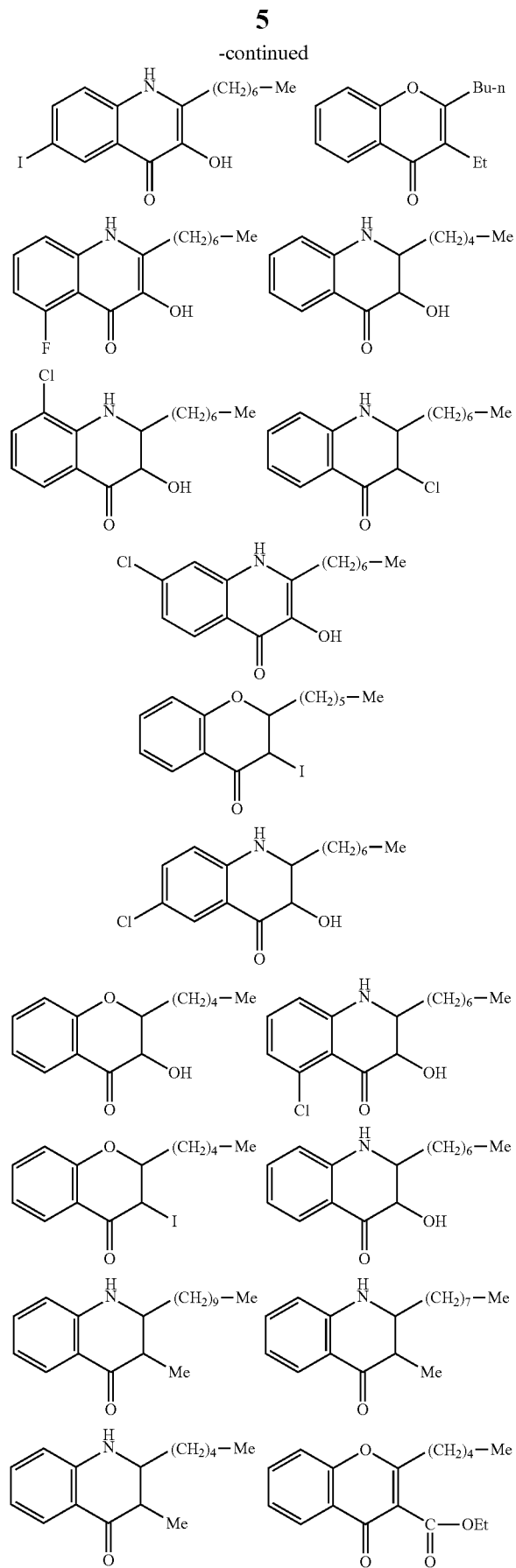
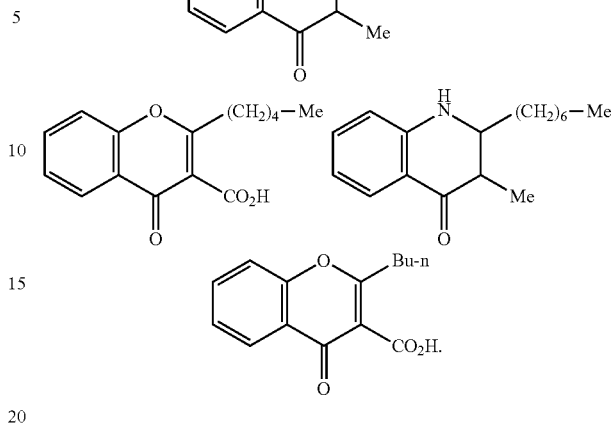

Compounds are usually described herein using standard nomenclature or the definitions presented below. For compounds having asymmetric centers, it should be understood that (unless otherwise specified) all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope (i.e., an atom having the same atomic number but a different mass number). By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic centers, have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

Certain compounds are described herein using a general formula that includes variables, e.g. A, $A^1$, $A^2$, and $A^3$, L, R, $R^1$, $R^2$, $R^3$, $R^4$, $R^5$ to $R^8$, $X^1$, $X^2$, $X^3$, Y, Z, etc. Unless otherwise specified, each variable within such a formula is defined independently of any other variable, and any variable that occurs more than one time in a formula is defined independently at each occurrence. Thus, for example, if a group, e.g. A, is shown to be substituted with 0-3 $R^3$, the group may be unsubstituted or substituted with 1, 2 or 3 $R^3$ groups, and $R^3$ at each occurrence is selected independently from the definition of $R^3$. Also, combinations of substituents and/or variables are permissible only if such combinations result in stable compounds, i.e., compounds that can be isolated, characterized and tested for biological activity.

As used herein a wording defining the limits of a range of length such as, e. g., "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range. For example, the term "$C_{1-6}$" (or "$C_1$-$C_6$") refers to 1 to 6, i.e. 1, 2, 3, 4, 5 or 6, carbon atoms.

A "pharmacologically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such pharmaceutical salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 4 (i.e., 0, 1, 2, 3, or 4) and the like. Similarly, pharmaceutically acceptable cations include, but are not limited to sodium, potassium, calcium, aluminum, lithium and ammonium. Those of ordinary skill in the art will recognize further pharmacologically acceptable salts for the compounds provided herein. In general, a pharmacologically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula (I) may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula I provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent," as used herein, refers to a molecular moiety that is covalently bonded to an atom within a molecule of interest. For example, a "ring substituent" may be a moiety such as a halogen, alkyl group, haloalkyl group, hydroxy, cyano, amino, nitro, mercapto, or other substituent described herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e. a compound that can be isolated, characterized and tested for biological activity. When a substituent is oxo (i.e., =O), then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

As used herein, "comprising", "including", "containing", "characterized by", and grammatical equivalents thereof are inclusive or open-ended terms that do not exclude additional, unrecited elements or method steps. "Comprising", etc. is to be interpreted as including the more restrictive term "consisting of".

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

In general, unless defined otherwise, technical and scientific terms used herein have the same meaning as commonly understood by one of ordinary skill in the art to which this invention belongs, and are consistent with general textbooks and dictionaries.

The expression "optionally substituted" refers to groups in which one or more hydrogen atoms have been replaced each independently of the others by hydrogen, fluorine, chlorine, bromine or iodine atoms or by OH, =O, SH, =S, $NH_2$, =NH, CN or $NO_2$ groups. This expression refers furthermore to groups in which one or more hydrogen atoms have been replaced each independently of the others by unsubstituted $C_1$-$C_6$alkyl, ($C_1$-$C_6$) haloalkyl (e.g. a fluoromethyl, trifluoromethyl, chloromethyl, (1- or 2-)haloethyl (e.g. (1- or 2-) chloroethyl), or (2- or 3-) halopropyl (e.g. (2- or 3-) fluoropropyl) group), ($C_1$-$C_6$) hydroxyalkyl (e.g. a hydroxymethyl, (1- or 2-)hydroxyethyl, or (2- or 3-) hydroxypropyl group), unsubstituted $C_2$-$C_6$alkenyl, unsubstituted $C_2$-$C_6$alkynyl, unsubstituted $C_1$-$C_6$heteroalkyl, unsubstituted $C_3$-$C_{10}$cycloalkyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl or unsubstituted $C_2$-$C_{11}$heteroaralkyl groups.

The expression alkyl refers to a saturated, straight-chain or branched hydrocarbon group that contains from 1 to 20 carbon atoms, preferably from 1 to 12 carbon atoms, more preferably from 1 to 6 carbon atoms, for example a methyl, ethyl, propyl, iso-propyl, n-butyl, iso-butyl, sec-butyl, tert-butyl, n-pentyl, n-hexyl, 2,2-dimethylbutyl or n-octyl group. The alkyl groups may optionally be substituted.

The expression "alkylene" (or alkanediyl functional group) refers to an unsubstituted, saturated, straight chain hydrocarbon group that contains the indicated number of carbon atoms (in the form of methylene ($CH_2$) groups) and has the free valencies at the terminal methylene groups, for example a butylene —$(CH_2)_4$—, n-pentylene —$(CH_2)_5$—, n-hexylene —$(CH_2)_6$—, or n-octylene —$(CH_2)_8$— group.

The expression alkenyl refers to an at least partially unsaturated, straight-chain or branched hydrocarbon group that contains one or more double bond(s) and from 2 to 20 carbon atoms, preferably from 2 to 12 carbon atoms, more preferably from 2 to 6 carbon atoms, for example an ethenyl (vinyl), propenyl (allyl), iso-propenyl, butenyl, isoprenyl or hex-2-enyl group. Preferably, an alkenyl group has one or two, especially one, double bond(s).

The expression "alkenylene" refers to an at least partially unsaturated alkanediyl functional group as defined above that contains one or more double bond(s) (i.e. the methylene groups of the alkanediyl functional group are interrupted by —CH=CH— and/or terminated by —CH$_2$—CH=).

The expression alkynyl refers to an at least partially unsaturated, straight-chain or branched hydrocarbon group that contains one or more triple bond(s) and from 2 to 20 carbon atoms, preferably from 2 to 12 carbon atoms, more preferably from 2 to 6, e.g. 2, 3 or 4, carbon atoms, for example an ethynyl (acetylenyl), propynyl, butynyl or propargyl group. Preferably, an alkynyl group has one or two, especially one, triple bond(s).

The expression "alkynylene" refers to an at least partially unsaturated alkanediyl functional group as defined above that contains one or more triple bond(s) (i.e. the methylene groups of the alkanediyl functional group are interrupted by —CH≡CH— and/or terminated by —CH$_2$—C≡).

As used herein, the expression "heteroalkyl" also includes heteroalkenyl and heteroalkynyl, and accordingly refers to an alkyl, alkenyl or alkynyl (straight chain or branched) group as defined above, in which one or more, preferably 1, 2, 3 or 4, carbon atoms have been replaced each independently of the others by an oxygen, nitrogen, phosphorus, boron, selenium, silicon or sulphur atom, preferably by an oxygen, sulphur or nitrogen atom, or by a SO or SO$_2$ group. As a result, the expression heteroalkyl also encompasses groups derived from a carboxylic acid, such as, for example, acyl, acylalkyl, alkoxycarbonyl, acyloxy, acyloxyalkyl, carboxyalkylamide or alkoxycarbonyloxy. Examples of heteroalkyl groups are alkylamino, dialkylamino, alkylaminoalkyl, dialkylaminoalkyl, acylalkyl, alkoxycarbonyl, alkylcarbamoyl, alkylamido, alkylcarbamoylalkyl, alkylamidoalkyl, alkylcarbamoyloxyalkyl, alkylureidoalkyl, alkoxycarbonyloxy, alkoxy, or alkoxyalkyl.

Further examples of heteroalkyl groups are groups of formulae: $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a direct bond, a $C_1$-$C_6$ alkylene, a $C_2$-$C_6$ alkenylene or a $C_2$-$C_6$ alkynylene group. Specific examples of heteroalkyl groups include acyl, methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, isopropylethylamino, methylaminomethyl, ethylaminomethyl, diisopropyl-aminoethyl, dimethylaminomethyl, dimethylaminoethyl, acetyl, propionyl, butyryloxy, acetyloxy, methoxycarbonyl, ethoxycarbonyl, isobutyrylamino-methyl, N-ethyl-N-methyl-carbamoyl, N-methylcarbamoyl, cyano, nitrile, isonitrile, thiocyanate, isocyanate, isothiocyanate and alkylnitrile.

The expression alkoxy refers to an alkyl group singular bonded to oxygen.

The expression alkylthio refers to an alkyl group singular bonded to sulfur.

The expression cycloalkyl refers to a saturated or partially unsaturated cyclic group that contains one or more rings (preferably 1 or 2), containing from 3 to 14 ring carbon atoms, preferably from 3 to 10 (more preferably 3, 4, 5, 6 or 7) ring carbon atoms. In an embodiment a partially unsaturated cyclic group has one, two or more double bonds, such as a cycloalkenyl group. Specific examples of a cycloalkyl group are a cyclopropyl, cyclobutyl, cyclopentyl, spirol[4,5]decanyl, norbornyl, cyclohexyl, cyclopentenyl, cyclohexadienyl, decalinyl, bicyclo-[4.3.0]nonyl, cyclopentylcyclohexyl, and a cyclohex-2-enyl group.

The expression heterocycloalkyl refers to a cycloalkyl group as defined above in which one or more, preferably 1, 2 or 3, ring carbon atoms have been replaced each independently of the others by an oxygen, nitrogen, or sulphur atom (preferably oxygen or nitrogen), or by a SO or SO2 group. A heterocycloalkyl group has preferably 1 or 2 ring(s) containing from 3 to 10 (more preferably 3, 4, 5, 6 or 7) ring atoms. Examples are a aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, tetrahydrofuranyl, thiolanyl, phospholanyl, silolanyl, azolyl, thiazolyl, isothiazolyl, imidazolidinyl, pyrazolidinyl, oxazolidinyl, isoxazolidinyl, thiazolidinyl, isothiazolidinyl, dioxolanyl, dithiolanyl, piperazinyl, morpholinyl, thiopmorpholinyl, trioxanyl, azepanyl, oxepanyl, thiepanyl, homopiperazinyl, or urotropinyl group. Further examples are a 2-pyrazolinyl group, and also a lactam, a lactone and a cyclic imide. The heterocycloalkyl group can be optionally substituted, and may be saturated or mono-, di- or tri-unsaturated. As a result, a group derived from a carbohydrate or saccharide, such as furanoses or pentoses, e.g. arabinose, ribose, xylose, lyxose or desoxyribose, or pyranoses/hexoses or derivatives thereof, e.g. allose, altrose, glucose, mannose, gulose, idose, galactose, talose, 6-carboxy-D-glucose, 6-carboxy-D-galactose, N-acetylchitosamine, glucosamine, N-acetylchondrosamin, fucose, rhamnose, chinovose, represents an optionally substituted heterocycloalkyl group.

The expression alkylcycloalkyl refers to a group containing both cycloalkyl and also an alkyl, alkenyl or alkynyl group in accordance with the above definitions, for example alkyl-cycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (preferably 3, 4, 5, 6 or 7) carbon atoms, and one or two alkyl, alkenyl or alkynyl groups having 1 or 2 to 6 carbon atoms, the cyclic groups being optionally substituted.

The expression heteroalkylcycloalkyl refers to alkylcycloalkyl groups as defined above in which one or more (preferably 1, 2 or 3) carbon atoms have been replaced each independently of the others by an oxygen, nitrogen, silicon, selenium, phosphorus or sulphur atom (preferably oxygen, sulphur or nitrogen). A heteroalkylcycloalkyl group preferably contains 1 or 2 ring systems having from 3 to 10 (preferably 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynyl-heterocycloalkyl, heteroalkylcycloalkyl, heteroalkylheterocycloalkyl and hetero-alkylheterocycloalkenyl, the cyclic groups being optionally substituted and saturated or mono-, di- or tri-unsaturated.

The expression aryl or Ar refers to an aromatic group that contains one or more rings containing from 6 to 14 ring carbon atoms, preferably from 6 to 10 (more preferably 6) ring carbon atoms. Examples are a phenyl, naphthyl, biphenyl, or indanyl group.

The expression heteroaryl refers to an aromatic group that contains one or more rings containing from 5 to 14 ring atoms, preferably from 5 to 10 (more preferably 5 or 6) ring atoms, and contains one or more (preferably 1, 2, 3 or 4) oxygen, nitrogen, phosphorus or sulphur ring atoms (preferably O, S or N). Examples are 2-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl.

The expression aralkyl refers to a group containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetralin, dihydronaphthalene, indanone, phenylcyclopentyl, cumene, cyclohexylphenyl, fluorene and indan. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced each independently of the others by an oxygen, nitrogen, silicon, selenium, phosphorus, boron or sulphur atom (preferably oxygen, sulphur or nitrogen), that is to say to groups containing both aryl or heteroaryl and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, 1, 2, 3 or 4 of those carbon atoms having been replaced each independently of the others by oxygen, sulphur or nitrogen atoms. Examples of heteroaralkyl groups are arylheteroalkyl, arylheterocycloalkyl, arylheterocycloalkenyl, arylalkylheterocyclo alkyl, arylalkenylheterocycloalkenyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylhetero alkylcyclo alkyl, heteroarylheteroalkylcycloalkenyl, heteroalkylheteroarylalkyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The expression "halogen" or "halogen atom" as preferably used herein means fluorine, chlorine, bromine, or iodine.

The activity and more specifically the bioactivity of the compounds according to the present invention can be assessed using appropriate assays known to those skilled in the art, e.g. in vitro or in vivo assays. For instance, the PqsR antagonistic activity may be determined by E. coli-based β-galactosidase reporter gene assay, or evaluated in PQS assay, pyocyanin virulence assay and biofilm assay, as provided in more detail in the Examples below.

In the compound according to the present invention the 5-membered aromatic fusion ring A, which may be mono- or disubstituted with $R^3$, can be a furo, thieno, pyrrolo, oxazolo, thiazolo, imidazo, or pyrazolo group; and the 6-membered aromatic fusion ring A, which may be mono-, di- or trisubstituted with $R^3$, can be a ring containing 6 carbon ring atoms or 1 to 3 N ring atom(s).

The compound of the present invention may be represented by the general formula (II):

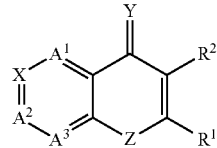

(II)

wherein
$A^1$, $A^2$, and $A^3$ each represents $CR^7$; or one of $A^1$, $A^2$, and $A^3$ represents N and the remaining two represent $CR^7$; or two of $A^1$, $A^2$, and $A^3$ represent N and the remaining represents $CR^7$;

X represents N or $CR^8$, with the proviso that X represents $CR^8$ if $A^1$ and $A^2$ or $A^2$ and $A^3$ represent N;

$R^7$ represents a hydrogen or halogen atom;

$R^8$ represents H, halogen atom, CN, $CF_3$, $NO_2$, $NH_2$, $NHC(=O)R^4$, $NHSO_2R^4$, $(CH_2)_mOR^4$, $SOCH_3$, SOCN, $SOCF_3$, $SO_2CH_3$, $SO_2CN$, $SO_2CF_3$, $SO_2NR^5R^6$, $C(=O)OC_{1-6}$ alkyl, $C(=O)NR^5R^6$, $COCH_3$, $COCF_3$, or $C(CN)_3$;

$R^1$, $R^2$, $R^4$, $R^5$, $R^6$, Y, Z and m are as defined in general formula (I) above.

Preferred is a compound of formula (II), or a pharmacologically acceptable salt thereof, wherein X is N; and $A^1$, $A^2$, and $A^3$ each represents $CR^7$.

Also preferred is a compound of formula (II), or a pharmacologically acceptable salt thereof, wherein X is $CR^8$; and $A^1$, $A^2$, and $A^3$ each represents $CR^7$.

Preferably, Y is O in the compound of formula (I) or (II).

Preferably, Z is NH or N—$C_{1-6}$ alkyl in the compound of formula (I) or (II), more preferably Z is NH.

Further preferred is a compound of formula (I), or a pharmacologically acceptable salt thereof, wherein the compound is represented by one of the following formulas:

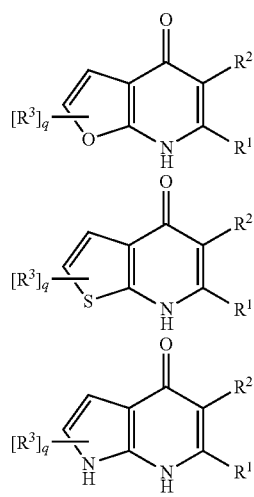

-continued

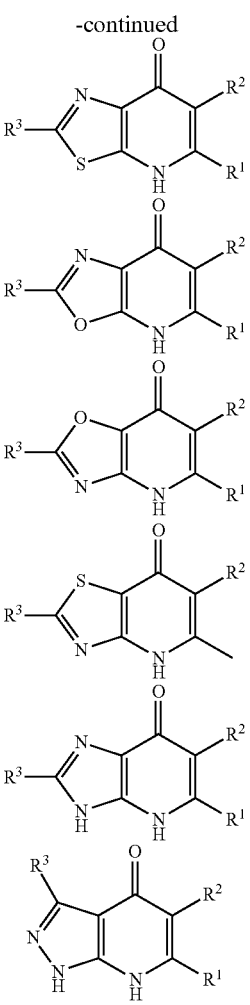

wherein $R^1$, $R^2$, and $R^3$ are defined as above; and q is 1 or 2.

In the compound of formula (I), including the above formulas, or formula (II), or a pharmacologically acceptable salt thereof, $R^1$ can represent a $C_6$- or $C_7$ alkyl group, in which one or two non-adjacent $CH_2$ groups may be replaced by O.

In the compound of formula (I), including the above formulas, or formula or (II), or a pharmacologically acceptable salt thereof, $R^1$ can be —$(CH_2)_6CH_3$; —$(CH_2)_4O(CH_2)CH_3$; or —$(CH_2)O(CH_2)_4CH_3$.

In the compound of formula (I), including the above formulas, or formula (II), or a pharmacologically acceptable salt thereof, $R^2$ can represent ($C_{1-3}$ alkyl)OH; ($C_{1-3}$ alkyl)O($C_{1-3}$ alkyl); —C(=O)O($CH_2$)$CH_3$; or —C(=O)NHOH.

Preferably, the compound of formula (I), including the above formulas, or formula (II), or a pharmacologically acceptable salt thereof, is selected from the group consisting of:

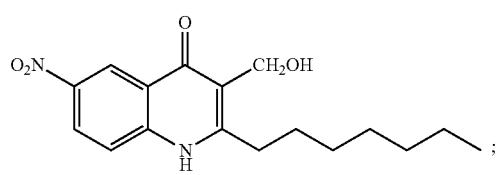

-continued

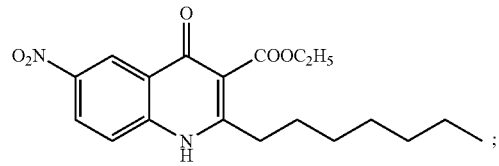

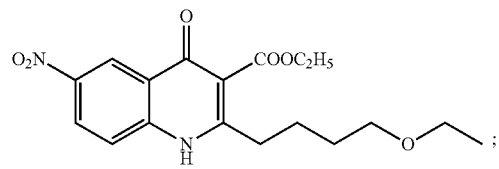

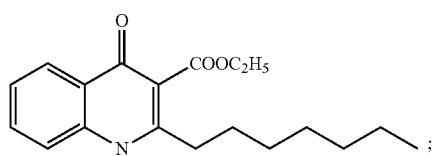

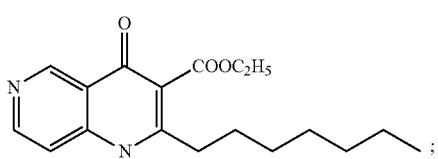

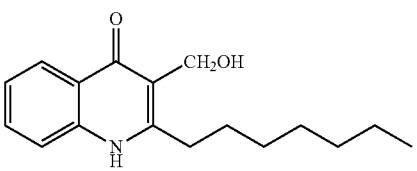

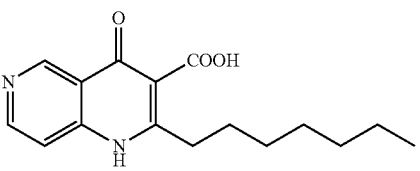

Further examples of the compound according to the invention include:

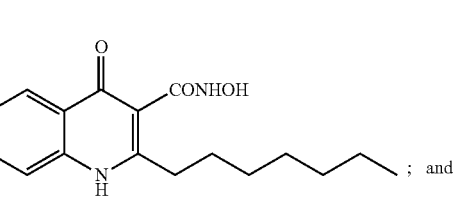

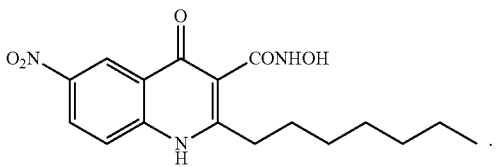

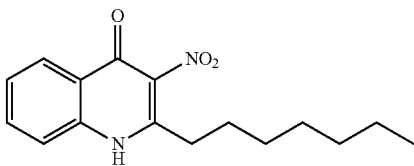

A compound of formula (I) or (II) can be obtained by chemical synthesis in a number of ways well known to one skilled in the art of organic synthesis using usual chemical reaction and synthesis methods. For example, the compounds can be obtained according to Reaction Schemes 1 to 3 shown below.

Reaction Scheme 1

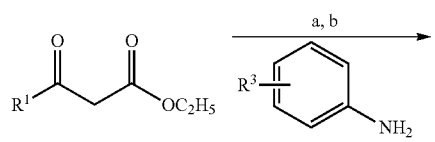

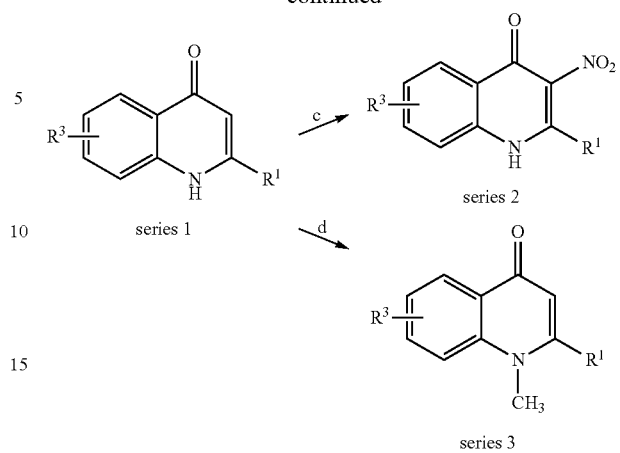

$R^1$ is as defined above, e.g. $C_4$—$C_{10}$alkyl, alkoxyl, $C_3H_6Ph$
$R^3$ is as defined above, e.g. H, halogen, CN, $CF_3$, $NO_2$
a) p-TsOH·$H_2O$, n-hexane, reflux; b) $Ph_2O$, reflux; c) conc. $HNO_3$, propionic acid, 110° C.; d) MeI, KOH, MeOH, r.t..

Reaction Scheme 2

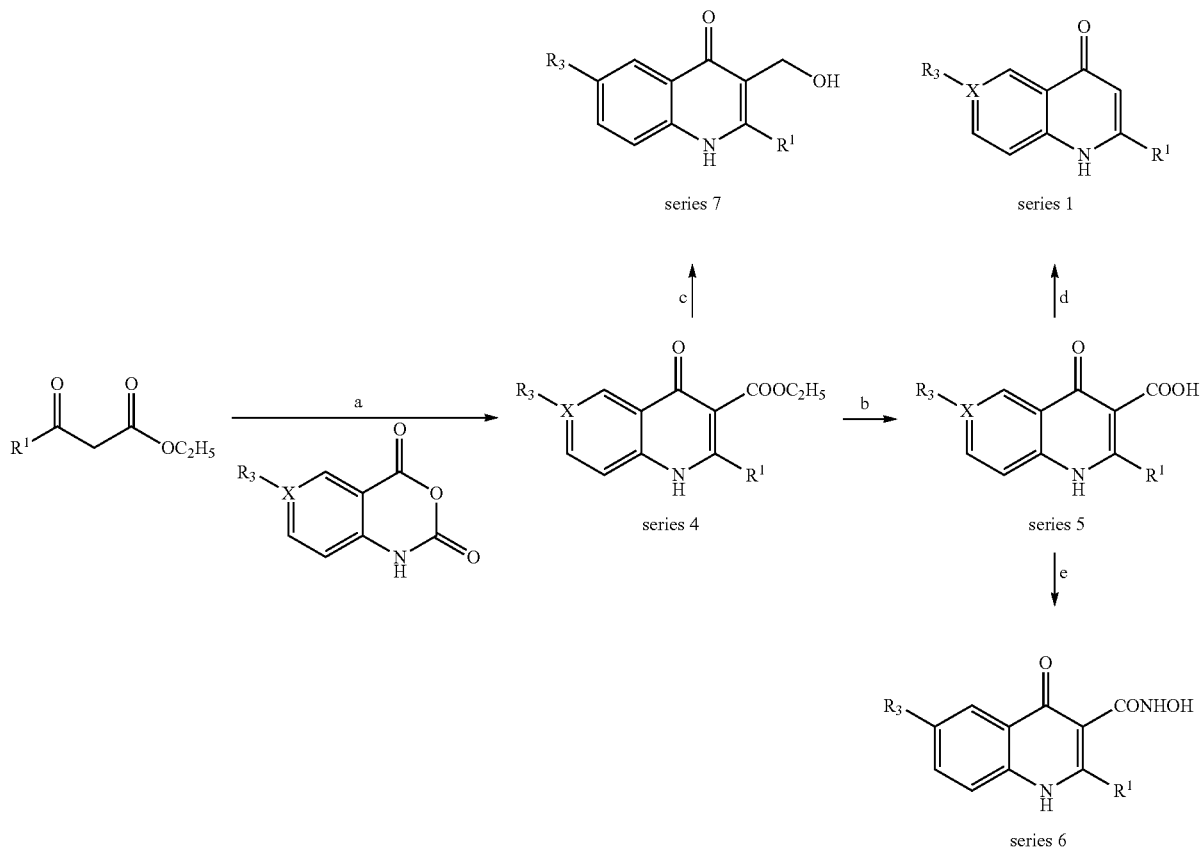

$R^1$ is as defined, e.g. alkyl, alkoxyl
$R^3$ is as defined, e.g. H, $NO_2$ or no atom (if X = N)
X = C, N
a) NaH, dry DMF, r.t. then HCl; b) NaOH, $H_2O$, reflux then HCl; c) LiAlH$_4$, dry THF, 0° C.-r.t.; d) 310° C.; e) N,N'-carbonyldiimidazole, N-methylmorpholine, $NH_2OH$·HCl, dry DMF, 0° C.-r.t..

Reaction Scheme 3

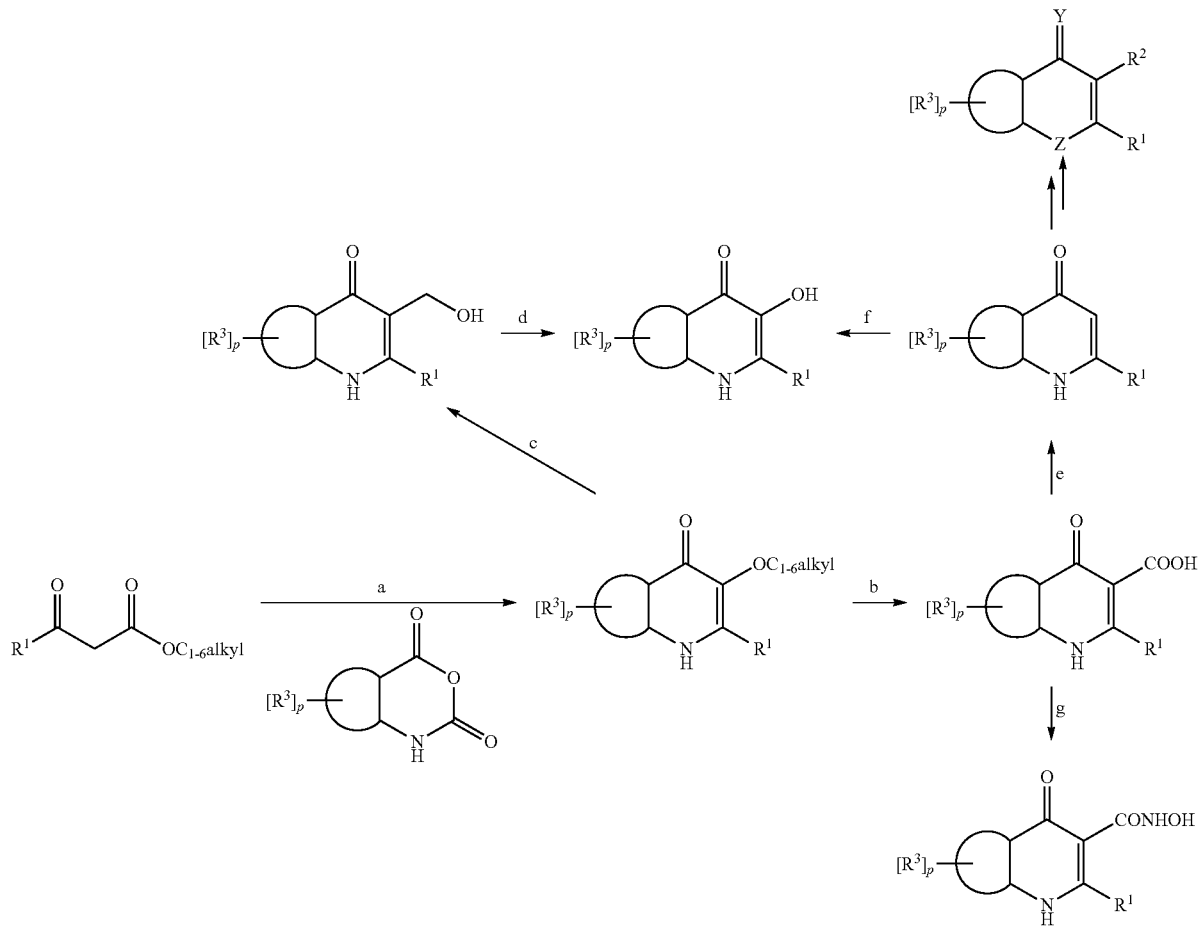

$R^1$, $R^2$, $R^3$, Z, Y, p were defined as above.
a) NaH, dry DMF, r.t. then HCl; b) NaOH, H$_2$O, reflux then HCl; c) LiAlH$_4$, dry THF, 0° C.-r.t.; d) MnO$_2$, dry THF, r.t. then B(OH)$_3$, conc. H$_2$SO$_4$, H$_2$O$_2$, THF, r.t.; e) 310° C.; f) hexamine, p-TsOH, AcOH, reflux, then HCl/water, then B(OH)$_3$, conc. H$_2$SO$_4$, H$_2$O$_2$, THF, r.t.; g) N,N'-carbonyldiimidazole, N-methylmorpholine, NH$_2$OH•HCl, dry DMF, 0° C.-r.t..

The therapeutic use of a compound of formula (I) or (II), its pharmacologically acceptable salts, solvates or hydrates and also formulations and pharmaceutical compositions which contain the same are within the scope of the present invention. Accordingly, the present invention relates to a compound or a pharmaceutical composition of the invention for use as a medicament. The present invention also relates to the use of those compounds of formula (I) or (II) as active ingredients in the preparation or manufacture of a medicament.

A pharmaceutical composition according to the present invention comprises at least one compound of formula (I) and, optionally, one or more carrier substance(s), excipient(s) and/or adjuvant(s). Pharmaceutical compositions may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Furthermore, one or more other active ingredients may (but need not) be included in the pharmaceutical compositions provided herein. For instance, the compounds of the invention may advantageously be employed in combination with another antibiotic or antifungal agent, an anti-viral agent, an antihistamine, a non-steroidal anti-inflammatory drug, a disease modifying anti-rheumatic drug, another cytostatic drug, a drug with smooth muscle activity modulatory activity or mixtures of the aforementioned.

Pharmaceutical compositions may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial and intraperitoneal injection, as well as any similar injection or infusion technique. Within the invention, compositions provided herein may be formulated as a lyophilizate. Formulation for topical administration may be preferred for certain conditions such as, e.g., in the treatment of skin conditions such as burns or itch.

Carrier substances are, for example, cyclodextrins such as hydroxypropyl β-cyclodextrin, micelles, liposomes, nanoparticles such as solid lipid nanoparticles, excipients and/or adjuvants. Customary excipients include, for example, inert diluents such as, e.g., calcium carbonate, sodium carbonate, lactose, calcium phosphate or sodium phosphate, granulating and disintegrating agents such as, e.g., corn starch or alginic acid, binding agents such as, e.g., starch, gelatin or acacia, and lubricating agents such as, e.g., magnesium stearate or stearic acid. Examples of adjuvants are aluminum hydroxide, aluminum phosphate, calcium phosphate hydroxide, paraffin oil, squalene, thimerosal, detergents, Freund's complete adjuvant, or Freund's incomplete adjuvant.

For the prevention and/or treatment of bacterial infections, especially *P. aeruginosa* or *Burkholderia* infections, the dose of the biologically active compound according to the invention may vary within wide limits and may be adjusted to individual requirements. Active compounds according to the present invention are generally administered in a therapeutically effective amount. The expression "therapeutically effective amount" denotes a quantity of the compound(s) that produces a result that in and of itself helps to ameliorate, heal, or cure the respective condition or disease. Preferred doses range from about 0.1 mg to about 140 mg per kilogram of body weight per day (about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient) and the severity of the particular disease undergoing therapy.

The invention further relates to a combination preparation containing at least one compound according to the invention and at least one further active pharmaceutical ingredient. The combination preparation of the invention for use as a medicament, in particular for use in the treatment or prophylaxis of bacterial infections, such as a *P. aeruginosa* or *Burkholderia* infection.

Preferably, in the combination preparation of the invention the further active pharmaceutical ingredient is another antibiotic, including classical antibiotics and anti-virulence compounds such as quorum sensing and adhesion inhibitors. The other antibiotic can be selected from the group consisting of β-lactam antibiotics, including penams, carbapenams, oxapenams, penems, carbapenems, monobactams, cephems, carbacephems, oxacephems, and monobactams; aminoglycoside antibiotics, including Amikacin, Arbekacin, Astromicin, Bekanamycin, Dibekacin, Framycetin, Gentamicin, Hygromycin B, Isepamicin, Kanamycin, Neomycin, Netilmicin, Paromomycin, Paromomycin sulfate, Ribostamycin, Sisomicin, Spectinomycin, Streptomycin, Tobramycin, and Verdamicin; and quinolone antibiotics, including Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Temafloxacin, and Trovafloxacin.

Preferred compounds of the invention will have certain pharmacological properties. Such properties include, but are not limited to oral bioavailability, such that the preferred oral dosage forms discussed above can provide therapeutically effective levels of the compound in vivo.

The compound according to the invention as well as the pharmaceutical composition according to the invention can be used as a medicament, which can be administered to a patient (e.g. parenterally to a human or another mammal), and will be present within at least one body fluid or tissue of the patient. As used herein, the term "treatment" encompasses both disease-modifying treatment and symptomatic treatment, either of which may be prophylactic, i.e., before the onset of symptoms, in order to prevent, delay or reduce the severity of symptoms, or therapeutic, i.e., after the onset of symptoms, in order to reduce the severity and/or duration of symptoms. In particular, the conditions or diseases that can be ameliorated, prevented or treated using a compound of formula (I) or a pharmaceutical composition according to the invention include bacterial infections, in particular antimicrobial activity against Gram-negative bacteria, especially infections with *Pseudomonas aeruginosa* strains (such as PAO1, PA14, MHH9639, MHH11444, and further clinical isolates exhibiting intact pqs QS system) including such of the urinary tract, of the gastrointestinal tract, of chronic and burnt wounds, of the eyes, of the ears, and of the lungs or infections with *Burkholderia* species (such as *B. cenocepacia* and *B. pseudomallei*). Accordingly, the present invention also provides methods for treating patients suffering from said diseases. Patients may include but are not limited to primates (especially humans), domesticated companion animals (such as dogs, cats, horses) and livestock (such as cattle, pigs, sheep), with dosages as described herein.

The invention further relates to coatings for medicinal devices, e.g. catheters, implants, or tubings, containing at least one compound according to the present invention.

BRIEF DESCRIPTION OF THE FIGURES

FIG. 1. Representative 3D biofilm projections of *P. aeruginosa* PA14 and the clinical isolate MHH9639. As can be taken from FIG. 1, compound 8 (depicted below) strongly inhibited the formation of biofilm.

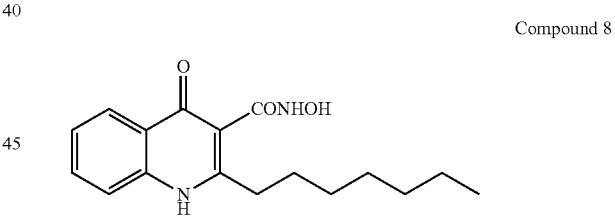

Compound 8

The present invention is now further illustrated by the following examples from which further features, embodiments and advantages of the present invention may be taken.

EXAMPLES

Materials and Methods
Chemicals and Analytical Methods Used for Organic Synthesis $^1$H and $^{13}$C NMR spectra were recorded on a Bruker DRX-500 instrument. Chemical shifts are given in parts per million (ppm) with the solvent resonance as internal standard for spectra obtained in CDCl$_3$, MeOH-d$_4$ and DMSO-d$_6$. All coupling constants (J) are given in hertz. Mass spectrometry (LC/MS) was performed on a MSQ® electro spray mass spectrometer (Thermo Fisher). The system was operated by the standard software Xcalibur®. A RP C18 NUCLEODUR® 100-5 (125×3 mm) column (Macherey-Nagel GmbH) was used as stationary phase with water/acetonitrile mixtures as eluent. All solvents were HPLC grade. Reagents were used as obtained from commercial suppliers without further purification. Flash chromatography was performed on silica gel 60, 70-230 mesh (Fluka) and the reaction progress was determined by thin-layer chromatography (TLC) analyses on silica gel 60, $F_{254}$ (Merck). Visualization was accomplished with UV light and staining with basic potassium permanganate ($KMnO_4$). The melting points were measured using melting point apparatus SMP3 (Stuart Scientific). The apparatus is uncorrected.

General Synthetic Methods for Series 1-7

Compounds were prepared according to the above Reaction Schemes 1 to 3 as described in the following.

Preparation of quinolin-4(1H)-one Derivative (Series 1/Method A)

A solution of β-ketoester (9.24 mmol, 1.0 equiv), aniline (9.24 mmol, 1.0 equiv) and p-TsOH.$H_2O$ (50 mg, 0.29 mmol, 3 mol %) in n-hexane (20 mL) was heated at reflux using a Dean-Stark separator for 5 h. After cooling the solution was concentrated under reduced pressure and the residue was added dropwise to refluxing (260° C.) diphenyl ether (5 mL). Refluxing was continued for 30 min After cooling to room temperature, diethyl ether (15 mL) was added and the mixture was left standing overnight at 5° C. The crystalline solid was isolated by filtration and washed with diethyl ether. The quinolin-4(1H)-one derivative was further purified by recrystallization from ethyl acetate or column chromatography on silica gel.

Preparation of 3-nitroquinolin-4(1H)-one Derivative (Series 2)

At 110° C. conc. $HNO_3$ (65% w/w, 15 µL, 0.30 mmol, 2.5 equiv) was added to a stirred suspension of quinolin-4(1H)-one derivative (series 1) (0.12 mmol, 1.0 equiv) in propionic acid (3 mL). The reaction mixture was heated for further 2 h with vigorous stirring. The resulting suspension was poured into ice. The product was isolated by filtration washed with cold water and dried under vacuum.

Preparation of 1-methylquinolin-4(1H)-one Derivative (Series 3)

Methyl iodide (3.24 mmol, 10.1 equiv) was added to a solution of quinolin-4(1H)-one derivative (series 1) (0.32 mmol, 1.0 equiv), KOH (56 mg, 1.00 mmol, 3.1 equiv) in methanol (1 mL) and the mixture was stirred over night at room temperature. After the precipitate was removed by filtration, the solvent was evaporated under reduced pressure. The 1-methylquinolin-4(1H)-one derivative was purified by column chromatography on silica gel (dichloromethane/methanol, 100/1).

Preparation of 4-oxo-1,4-dihydroquinoline-3-ester Derivative (Series 4)

Under nitrogen atmosphere β-ketoester (15 mmol, 1.0 equiv) was added to a suspension of sodium hydride (50-65% w/w, 0.72 g, 15 mmol, 1.0 equiv) in dry DMF (50 mL), causing the liberation of hydrogen gas. A solution of isatoic anhydride derivative (15 mmol, 1.0 equiv) in dry DMF (30 mL) was added dropwise and stirred overnight. Most of the solvent was removed under reduced pressure and the remaining solvent treated with 1M HCl, yielding the crude product as a yellow solid. The 4-oxo-1,4-dihydroquinoline-3-ester derivative was purified by recrystallization from ethyl acetate/methanol or column chromatography on silica gel.

Preparation of 4-oxo-1,4-dihydroquinoline-3-carboxylic acid Derivative (Series 5)

The 4-oxo-1,4-dihydroquinoline-3-ester derivative (series 4) was suspended in 10% NaOH solution and heated at reflux for 4 h. After cooling to 0° C. on an ice water bath and extraction with ethyl acetate, the water phase was acidified with conc. HCl to reach a pH of 4.0-6.0. The 4-oxo-1,4-dihydroquinoline-3-carboxylic acid was isolated by filtration, washed with water and dried under vacuum.

Preparation of quinolin-4(1H)-one Derivative (Series 1/Method B)

4-oxo-1,4-dihydroquinoline-3-carboxylic acid derivative (series 5) (0.45 mmol) was carefully purged with nitrogen under stirring, then slowly heated past its melting point to 310° C. under inert atmosphere with continued stirring for 8 min. The reaction was cooled to room temperature after the evident evolution of carbon dioxide ceased. The resulting solid was dissolved in a dichloromethane/methanol (15/1) solution. Insoluble material was removed by filtration and the solvents were removed under reduced pressure. The residue was purified by column chromatography on silica gel (dichloromethane/methanol, 60/1) to give quinolin-4 (1H)-one derivative.

Preparation of N-hydroxy-4-oxo-1,4-dihydroquinoline-3-carboxamide Derivative (Series 6)

A mixture of 4-oxo-1,4-dihydroquinoline-3-carboxylic acid derivative (series 5) (0.19 mmol, 1.0 equiv), N,N'-carbonyldiimidazole (62 mg, 0.38 mmol, 2.0 equiv) and dry DMF (2 mL) was stirred for 3 h at 75° C. The solution was cooled to 0° C. and a mixture of N-methylmorpholine (184 mg, 1.80 mmol, 10 equiv), hydroxylammonium chloride (130 mg, 1.90 mmol, 10 equiv) and dry DMF (1 mL) was added and the mixture was stirred overnight at room temperature. The solvent was removed under reduced pressure and the residue was purified by column chromatography on silica gel (dichloromethane/methanol, 40/1) to give N-hydroxy-4-oxo-1,4-dihydroquinoline-3-carboxamide derivative.

Preparation of 3-(hydroxymethyl)quinolin-4(1H)-one Derivative (Series 7)

At 0° C. $LiAlH_4$ (120 mg, 3.16 mmol, 2.0 equiv) was added to a stirred solution of 4-oxo-1,4-dihydroquinoline-3-ester derivative (series 4) (1.59 mmol, 1.0 equiv) in dry THF (30 mL). After stirring at room temperature for 2 h ethyl acetate (10 mL) was added at 0° C. and after filtration the solvent was removed under reduced pressure. The residue was purified by column chromatography (dichloromethane/methanol, 40/1) to give 3-(hydroxymethyl)quinolin-4 (1H)-one derivative.

Preparation of Example Compounds

Synthesis of 2-heptyl-3-(hydroxymethyl)-6-nitroquinolin-4(1H)-one (Compound 1) from Series 7

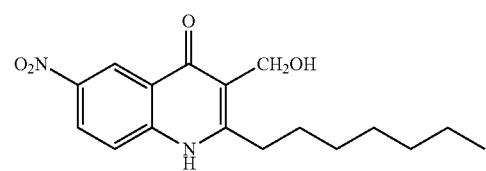 [SMILES: CCCCCCCc1[nH]c2ccc([N+](=O)[O-])cc2c(=O)c1CO]

The title compound was obtained according to preparation of 3-(hydroxymethyl)quinolin-4(1H)-one derivative (series 7) from ethyl 2-heptyl-6-nitro-4-oxo-1,4-dihydroquinoline-3-carboxylate (420 mg, 1.17 mmol). The product was isolated as a yellow solid (35 mg, 0.11 mmol, 9%), mp>350° C. $^1$H-NMR (500 MHz, DMSO-d$_6$): δ=0.86 (t, J=7.0 Hz, 3H), 1.23-1.42 (m, 8H), 1.70 (quint, J=7.5 Hz, 2H), 2.77 (t, J=7.5 Hz, 2H), 4.48 (d, J=5.5 Hz, 2H), 4.68 (t, J=5.5 Hz, 1H), 7.70 (d, J=9.0 Hz, 1H), 8.39 (dd, J=2.5, 9.0 Hz, 1H), 8.84 (d, J=3.0 Hz, 1H), 11.93 (br, 1H). $^{13}$C-NMR (125 MHz, DMSO-d$_6$): δ=13.9, 22.0, 28.4, 29.0, 29.2, 31.1, 53.4, 119.6, 119.9, 121.9, 122.9, 125.6, 142.3, 143.2, 153.9, 175.6. LC/MS: m/z 319.06 [M+H]$^+$, 99.9%.

Synthesis of ethyl 2-heptyl-6-nitro-4-oxo-1,4-dihydroquinoline-3-carboxylate (Compound 2) from Series 4

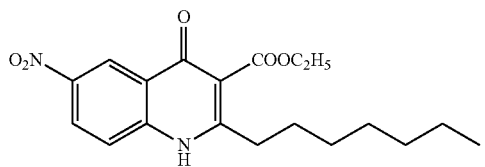

The title compound was obtained according to preparation of 4-oxo-1,4-dihydroquinoline-3-ester derivative (series 4) from 6-nitro-1H-benzo[d][1,3]oxazine-2,4-dione (3.0 g, 14 mmol, 0.9 equiv) and ethyl 3-oxodecanoate (3.2 g, 15 mmol, 1.0 equiv). The product was isolated as a yellow solid (1.8 g, 5.71 mmol, 41%). mp 239.6-241.8° C. $^1$H-NMR (500 MHz, MeOH-d$_4$): δ=0.91 (t, J=7.0 Hz, 3H), 1.29-1.47 (m, 11H), 1.78 (quint, J=7.5 Hz, 2H), 2.80 (t, J=8.0 Hz, 2H), 4.39 (q, J=8.0 Hz, 2H), 7.72 (d, J=9.0 Hz, 1H), 8.49 (dd, J=2.5, 9.0 Hz, 1H), 9.04 (d, J=2.5 Hz, 1H). $^{13}$C-NMR (125 MHz, MeOH-d$_4$): δ=14.4, 14.6, 23.3, 30.3, 30.5, 30.6, 32.8, 33.8, 62.6, 117.6, 120.8, 123.1, 125.4, 127.8, 144.3, 145.4, 156.8, 167.8, 176.4. LC/MS: m/z 360.77 [M+H]$^+$, 96.3%.

Synthesis of 2-heptyl-3-nitroquinolin-4(1H)-one (Compound 9) from Series 2

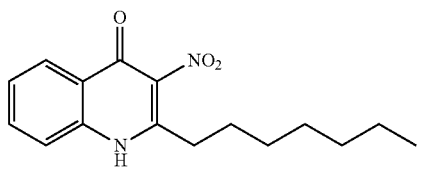 [SMILES: CCCCCCCc1[nH]c2ccccc2c(=O)c1[N+](=O)[O-]]

The title compound was obtained according to preparation of 3-nitroquinolin-4(1H)-one derivative (series 2) from 2-heptylquinolin-4(1H)-one (30 mg, 0.12 mmol). The product was isolated as a yellow solid (12 mg, 0.04 mmol, 33%), mp 258.0-259.1° C. $^1$H-NMR (500 MHz, DMSO-d$_6$): δ=0.85 (t, J=6.5 Hz, 3H), 1.25-1.34 (m, 8H), 1.70 (quint, J=7.5 Hz, 2H), 2.73 (t, J=7.5 Hz, 2H), 7.45 (t, J=7.5 Hz, 1H), 7.66 (d, J=7.5 Hz, 1H), 7.78 (t, J=7.5 Hz, 1H), 8.15 (d, J=8.0 Hz, 1H), 12.32 (br, 1H). $^{13}$C-NMR (125 MHz, DMSO-d$_6$): δ=13.9, 22.0, 28.1, 28.4, 28.6, 30.3, 31.0, 118.7, 124.8, 125.2, 125.3, 133.2, 135.6, 138.6, 149.4, 167.5. LC/MS: m/z 289.00 [M+H]$^+$, 96.7%.

Synthesis of 2-heptyl-N-hydroxy-6-nitro-4-oxo-1,4-dihydroquinoline-3-carboxamide (Compound 10) from Series 6

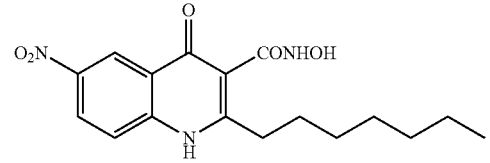

The title compound was obtained according to preparation of N-hydroxy-4-oxo-1,4-dihydroquinoline-3-carboxamide derivative (series 6) from 2-heptyl-6-nitro-4-oxo-1,4-dihydroquinoline-3-carboxylic acid (250 mg, 0.75 mmol). The product was isolated as a yellow solid (38 mg, 0.11 mmol, 15%), mp 200.9-202.8° C. $^1$H-NMR (500 MHz, DMSO-d$_6$): δ=0.86 (t, J=7.0 Hz, 3H), 1.26-1.37 (m, 8H), 1.69 (quint, J=7.5 Hz, 2H), 2.80 (t, J=7.5 Hz, 2H), 7.76 (d, J=9.5 Hz, 1H), 8.45 (dd, J=3.0, 9.5 Hz, 1H), 8.84 (d, J=2.5 Hz, 1H), 9.06 (s, 1H), 11.00 (s, 1H), 12.28 (br, 1H). $^{13}$C-NMR (125 MHz, DMSO-d$_6$): δ=13.9, 22.0, 28.3, 29.0, 29.1, 31.1, 32.2, 115.4, 120.0, 121.7, 123.6, 126.4, 142.8, 143.0, 155.8, 162.4, 174.3. LC/MS: m/z 348.00 [M+H]$^+$, 98.5%.

Synthesis of 2-heptyl-6-nitro-4-oxo-1,4-dihydroquinoline-3-carboxylic acid (Compound 12) from Series 5

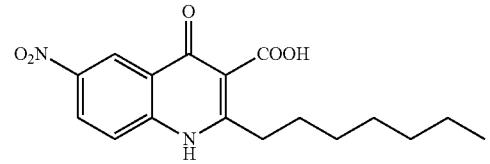 [SMILES: CCCCCCCc1[nH]c2ccc([N+](=O)[O-])cc2c(=O)c1C(=O)O]

The title compound was obtained according to preparation of 4-oxo-1,4-dihydroquinoline-3-carboxylic acid derivative (series 5) from ethyl 2-heptyl-6-nitro-4-oxo-1,4-dihydroquinoline-3-carboxylate (250 mg, 0.69 mmol). The product was isolated as a gray solid (32 mg, 0.10 mmol, 14%). mp 192.7-194.9° C. $^1$H-NMR (500 MHz, DMSO-d$_6$): δ=0.86 (t, J=7.0 Hz, 3H), 1.27-1.44 (m, 8H), 1.67 (quint, J=7.5 Hz, 2H), 3.26 (t, J=7.5 Hz, 2H), 7.91 (d, J=9.0 Hz, 1H), 8.58 (dd, J=2.5, 9.0 Hz, 1H), 8.90 (d, J=2.5 Hz, 1H), 13.22 (br, 1H), 15.64 (br, 1H). $^{13}$C-NMR (125 MHz, DMSO-d$_6$): δ=13.9, 22.0, 28.3, 29.1, 31.1, 33.3, 107.6, 120.8, 121.5, 122.7, 127.7, 141.6, 144.2, 163.9, 165.4, 178.6. LC/MS: m/z 332.90 [M+H]$^+$, 98.8%.

Synthesis of 2-heptyl-1-methyl-6-(trifluoromethyl)quinolin-4(1H)-one (Compound Ref. 1) from Series 3

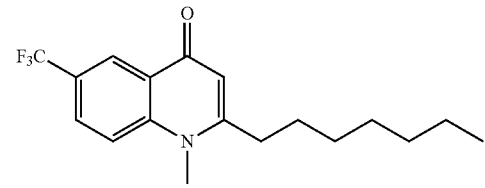 [SMILES: CCCCCCCc1cc(=O)c2cc(C(F)(F)F)ccc2n1C]

The title compound was obtained according to preparation of 1-methylquinolin-4(1H)-one derivative (series 3) from methyl iodide (0.46 g, 3.24 mmol, 10.1 equiv) and 2-heptyl-6-(trifluoromethyl)quinolin-4(1H)-one (100 mg, 0.32 mmol, 1.0 equiv). The product was isolated as a white solid (25 mg, 0.08 mmol, 25%), mp 125.1-126.3° C. $^1$H-NMR (500 MHz, MeOH-d$_4$): δ=0.92 (t, J=7.0 Hz, 3H), 1.31-1.53 (m, 8H), 1.74 (quint, J=7.5 Hz, 2H), 2.90 (t, J=7.5 Hz, 2H), 3.92 (s, 3H), 6.35 (s, 1H), 7.99-8.04 (m, 2H), 8.59-8.60 (m, 1H). $^{13}$C-NMR (125 MHz, MeOH-d$_4$): δ=14.4, 23.7, 29.6, 30.1, 30.3, 32.9, 35.6, 35.7, 112.1, 119.4, 124.4 (q, J$_{CF}$=4 Hz), 125.5 (q, J$_{CF}$=270 Hz), 126.6, 126.7 (q, J$_{CF}$=33 Hz), 129.5 (q, J$_{CF}$=3 Hz), 145.3, 160.0, 178.9. LC/MS: m/z 325.79 [M+H]$^+$, 99.9%.

Synthesis of 2-(Pentyloxymethyl)-6-(trifluoromethyl)quinolin-4(1H)-one (Compound Ref. 4) from Series 1

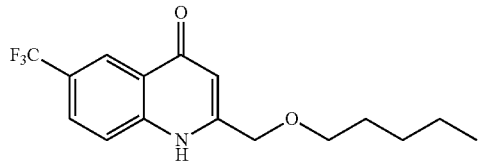 [SMILES: CCCCCOCc1cc(=O)c2cc(C(F)(F)F)ccc2[nH]1]

The title compound was prepared according to preparation of quinolin-4(1H)-one derivative (series 1/method A) from ethyl 3-oxo-4-(pentyloxy) butanoate (2.16 g, 10 mmol) and 4-(trifluoromethyl) aniline (1.61 g, 10 mmol). The product was isolated as a white solid (1.51 g, 4.82 mmol, 48%), mp 215.8-216.5° C. $^1$H-NMR (500 MHz, DMSO-d$_6$): δ=0.85 (t, J=7.1 Hz, 3H), 1.24-1.33 (m, 4H), 1.57 (quint, J=6.9 Hz, 2H), 3.49 (t, J=6.6 Hz, 2H), 4.48 (s, 2H), 6.18 (s, 1H), 7.82 (d, J=8.8 Hz, 1H), 7.93 (dd, J=8.8, 2.2 Hz, 1H), 8.32 (d, J=1.6 Hz, 1H), 11.93 (br, 1H). $^{13}$C-NMR (125 MHz, DMSO-d$_6$): δ=13.8, 21.9, 27.7, 28.7, 68.5, 70.3, 108.0, 119.9, 122.4 (q, J$_{CF}$=4 Hz), 123.2 (q, J$_{CF}$=32 Hz), 124.1, 124.2 (q, J$_{CF}$=272 Hz), 127.6 (q, J$_{CF}$=3 Hz), 142.3, 150.8, 176.3. LC/MS: m/z 313.97 [M+H]$^+$, 96.1%.

Synthesis of 2-Heptyl-1,6-naphthyridin-4(1H)-one (Compound Ref. 9) from Series 1

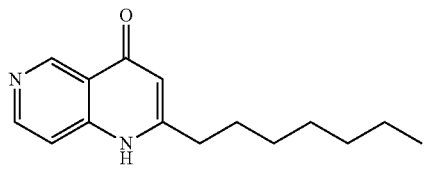 [SMILES: CCCCCCCc1cc(=O)c2cnccc2[nH]1]

The title compound was obtained according to preparation of quinolin-4(1H)-one derivative (series 1/method B) from 2-heptyl-4-oxo-1,4-dihydro-1,6-naphthyridine-3-carboxylic acid (292 mg, 1.01 mmol). The product was isolated as a gray solid (150 mg, 0.61 mmol, 60%), mp 132.5-133.0° C. $^1$H-NMR (500 MHz, DMSO-d$_6$): δ=0.85 (t, J=7.0 Hz, 3H), 1.25-1.31 (m, 8H), 1.66 (quint, J=7.5 Hz, 2H), 2.58 (t, J=7.5 Hz, 2H), 6.04 (s, 1H), 7.40 (d, J=5.5 Hz, 1H), 8.55 (d, J=5.5 Hz, 1H), 9.13 (s, 1H), 11.71 (br, 1H). $^{13}$C-NMR (125 MHz, DMSO-d$_6$): δ=13.9, 22.0, 28.0, 28.3, 28.4, 31.1, 33.2, 110.6, 111.8, 119.4, 144.6, 148.7, 149.7, 155.1, 176.7. LC/MS: m/k 245.01 [M+H]$^+$, 98.6%.

Chemicals, Bacterial Strains and Media Used in Biological Experiments

Yeast extract was purchased from Fluka (Neu-Ulm, Germany), peptone from casein from Merck (Darmstadt, Germany), and Bacto™ Tryptone from BD Biosciences (Heidelberg, Germany). Salts and organic solvents of analytical grade were obtained from VWR (Darmstadt, Germany).

*P. aeruginosa* strain PA14 (PA14) was stored in glycerol stocks at −80° C.

The following media were used: Luria Bertani broth (LB) and PPGAS medium [23].

Reporter Gene Assay in *E. coli*

The ability of the compounds to either stimulate or antagonize the PqsR-dependent transcription was analysed as previously described [19] using a β-galactosidase reporter gene assay in *E. coli* expressing PqsR. Briefly, a culture of *E. coli* DH5α cells containing the plasmid pEAL08-2, which encodes PqsR under the control of the tac promoter and the β-galactosidase reporter gene lacZ controlled by the pqsA promoter, were co-incubated with test compound. Antagonistic effects of compounds were assayed in the presence of 50 nM PQS. After incubation, β-galactosidase activity was measured spectralphotometrically at OD$_{420\ nm}$ using POLARstar Omega (BMG Labtech, Ortenberg, Germany) and expressed as percent stimulation of controls. For the determination of IC$_{50}$ values, compounds were tested at least at eight different concentrations.

Results of tests using the above reporter gene assay are presented in Table 1 below.

TABLE 1

Determination of antagonistic activity of compounds in *E. coli*-based reporter gene assay.

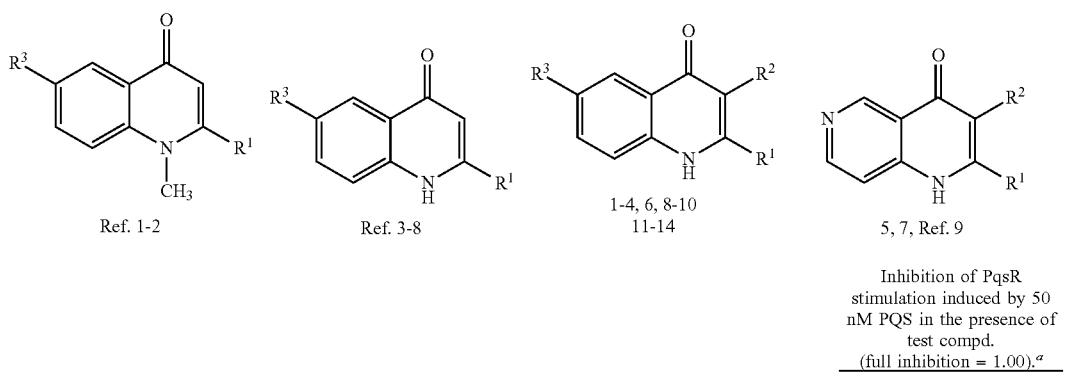

| compd. | R$^1$ | R$^2$ | R$^3$ | Inhibition of PqsR stimulation induced by 50 nM PQS in the presence of test compd. (full inhibition = 1.00).$^a$ | |
|---|---|---|---|---|---|
| | | | | 50 nM | 5 μM |
| Ref. 1* | n-C$_7$H$_{15}$ | — | CF$_3$ | 0.31 | 1.00 |
| Ref. 2 | n-C$_6$H$_{13}$ | — | CF$_3$ | 0.45 | 1.00 |
| Ref. 3 | CH$_2$OC$_5$H$_{11}$ | — | H | 0.11 | 0.06 |

TABLE 1-continued

Determination of antagonistic activity of compounds in E. coli-based reporter gene assay.

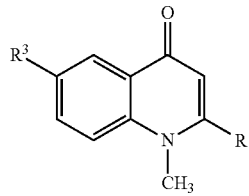
Ref. 1-2

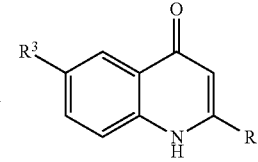
Ref. 3-8

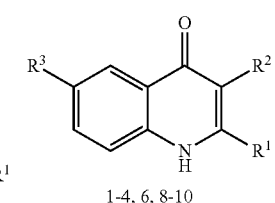
1-4, 6, 8-10
11-14

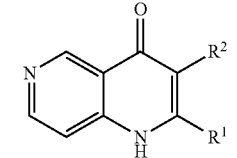
5, 7, Ref. 9

| | | | | Inhibition of PqsR stimulation induced by 50 nM PQS in the presence of test compd. (full inhibition = 1.00).[a] | |
|---|---|---|---|---|---|
| compd. | $R^1$ | $R^2$ | $R^3$ | 50 nM | 5 µM |
| Ref. 4 | $CH_2OC_5H_{11}$ | — | $CF_3$ | 0.29 | 1.00 |
| Ref. 5 | $CH_2OC_5H_{11}$ | — | $NO_2$ | 0.49 | 1.00 |
| Ref. 6 | $C_4H_8OC_2H_5$ | — | H | 0.54 | 0.42 |
| Ref. 7 | $C_4H_8OC_2H_5$ | — | $CF_3$ | 0.08 | 0.69 |
| Ref. 8 | $C_4H_8OC_2H_5$ | — | $NO_2$ | 0.06 | 0.72 |
| Ref. 9 | n-$C_7H_{15}$ | H | — | 0.08 | 0.02 |
| 1 | n-$C_7H_{15}$ | $CH_2OH$ | $NO_2$ | 0.45 | 1.00 |
| 2 | n-$C_7H_{15}$ | $COOC_2H_5$ | $NO_2$ | −0.08 | 0.20 |
| 3 | $C_4H_8OC_2H_5$ | $COOC_2H_5$ | $NO_2$ | 0.02 | 0.27 |
| 4 | n-$C_7H_{15}$ | $COOC_2H_5$ | H | 0.18 | 0.32 |
| 5 | n-$C_7H_{15}$ | $COOC_2H_5$ | — | 0.24 | 0.76 |
| 6 | n-$C_7H_{15}$ | $CH_2OH$ | H | 0.05 | 0.28 |
| 7 | n-$C_7H_{15}$ | COOH | — | 0.06 | 0.20 |
| 8 | n-$C_7H_{15}$ | CONHOH | H | 0.15 | 0.29 |
| 9 | n-$C_7H_{15}$ | $NO_2$ | H | 0.14 | 0.17 |
| 10 | n-$C_7H_{15}$ | CONHOH | $NO_2$ | 0.30 | 0.78 |
| 11 | $CH_2OC_5H_{11}$ | $COOC_2H_5$ | $NO_2$ | 0.02 | 0.13 |
| 12 | n-$C_7H_{15}$ | COOH | $NO_2$ | 0.11 | 0.34 |
| 13 | $CH_2OC_5H_{11}$ | COOH | $NO_2$ | 0.07 | 0.06 |
| 14 | $C_4H_8OC_2H_5$ | COOH | $NO_2$ | 0.01 | 0.33 |

[a]β-Galactosidase reporter gene assay was performed in E. coli transformed with plasmid pEAL08-2 encoding PqsR and reporter gene lacZ controlled by pqsA promoter. Mean value of at least two independent experiments with n = 4, standard deviation less than 25%.
*Ref. 1-9 represent structurally or functionally related reference compounds or synthetic intermediates of compounds of the invention.

Determination of Extracellular PQS Levels

Quantification of PQS produced by P. aeruginosa PA14 was performed according to the method of Maurer et al. [15]. For each sample, cultivation and sample work-up were performed in triplicates. Inhibition values of PQS formation were normalized to $OD_{600}$.

Pyocyanin Assay

For analysis of pyocyanin formation, cultivation procedure was the same as for HHQ determination with the exception of using PPGAS medium. Pyocyanin produced by PA14 was quantified using the method of Essar et al. [24] with some modifications, as described in detail by Klein et al. [17]. Briefly, 900 µL of each culture were extracted with 900 µL of chloroform and 800 µL of the organic phase re-extracted with 250 µL of 0.2 M HCl. $OD_{520}$ was measured in the aqueous phase using FLUOstar Omega (BMG Labtech, Ortenberg, Germany). For each sample, cultivation and sample work-up were performed in triplicates. Inhibition values of pyocyanin formation were normalized to $OD_{600}$.

Biofilm Growth Assay

Static biofilms at the bottom of 96 well microtiter plates were grown with small modifications as previously described [25, 26]. In brief, overnight P. aeruginosa LB cultures of PA14 were adjusted to an OD600 of 0.002 with fresh medium and transferred into a half-area 96 well µClear plate (Greiner Bio-One, 100 µL/well). The plate was covered with an air-permeable foil and incubated at 37° C. in a chamber with humid atmosphere. After 24 h, a staining solution including Syto9 and propidium iodide (LIVE/DEAD BacLight Bacterial Viability kit, Molecular Probes/Invitrogen) and the test compound solved in DMSO was added to the biofilms (final concentration 100 µM, 1% DMSO (v/v)) and biofilms were further incubated for 24 h at 37° C. After in total 48 h, biofilm stacks were acquired in the center of each well (step size: 3 µm) using an automated confocal microscope (TCS SP8, Leica Microsystems) equipped with an ×40/1.10 water objective. The acquired image stacks were processed and analyzed with a customized analysis solution for the Developer XD2 (Definiens) based on a previously described algorithm [27]. 3D-projections of the biofilms are visualized with the software IMARIS (version 7.6.5, Bitplane).

Test of Anti-Virulence Properties

The anti-virulence properties of compounds according to the invention were tested by determining the reduction of PQS and pyocyanin levels in P. aeruginosa. The corresponding test assays were performed as described above. The results are shown in Table 2 below.

TABLE 2

Determination of the reduction of PQS and pyocyanin levels in *P. aeruginosa* for selected compounds

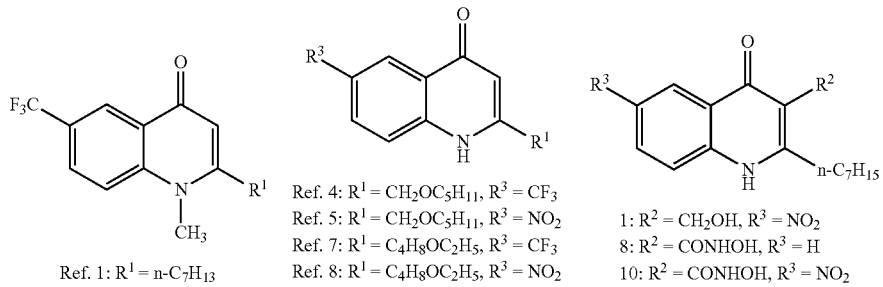

| Compd. | PQS$^a$ | Pyocyanin$^a$ |
|---|---|---|
| Ref. 1* | 8.9 | 58 |
| Ref. 4 | 21 | 29 |
| Ref. 5 | 23 | 27 |
| Ref. 7 | 8.6$^c$ | 39$^c$ |
| Ref. 8 | 13$^d$ | 23$^d$ |
| 1 | 33 | 83 |
| 8 | n.d.$^b$ | 51$^e$ |
| 10 | n.d.$^b$ | 57$^e$ |

Reduction with compd. at 15μM, [%]

$^a$PQS and pyocyanin assays were performed in *P. aeruginosa* PA14. Mean value of at least two independent experiments with n = 3, standard deviation less than 25%.
$^b$not determined.
$^{c, d, e}$determined at 250 μM, 100 μM and 12.5 μM, respectively.
*Ref. represent structurally or functionally related reference compounds or synthetic intermediates of compounds of the invention.

As can be taken from Table 2, compound 8 was able to strongly reduce the production of the virulence factor pyocyanin in *P. aeruginosa* PA14 (IC$_{50}$: ~12 μM). This implicates that the compound is a strong anti-virulence agent in vivo, as reduction of pyocyanin formation correlates with an enhanced survival of *P. aeruginosa*-infected *Caenorhabditis elegans* worms as well as *Galleria mellonella* larvae, two well established in vivo models for *P. aeruginosa* pathogenicity [20].

Test of Biofilm Formation Inhibitory Activity

As it was shown that a pqs QS-deficient mutant of *P. aeruginosa* having a transposon insertion within the pqsA gene forms less biofilm than the wild type, we tested the influence of compound 8 for its potential to interfere with biofilm formation by *P. aeruginosa* PA14 and the clinical isolate MHH9639. The latter was shown to produce similar amounts of PQS as strain PA14 (unpublished data) proving that the isolate possesses an intact pqs QS system. Indeed, we found that addition of compound 8 to 24 h old biofilms markedly reduced the biovolume of the biofilms of both *P. aeruginosa* strains. The results are shown in FIG. 1. Thus, compound 8, as an example for the whole ensemble of compounds belonging to the present invention, has proven promising for anti-biofilm therapy.

Overall, compound 8, as an example for the compounds of invention, has proven to be a promising anti-pathogenic compound exhibiting both anti-virulence and anti-biofilm activity allowing for an effective treatment of bacterial infections.

REFERENCES

1. Frei R, Breitbach A S, Blackwell H E (2012) Angew Chem Int Ed Engl 51:5226-5229
2. Yang L, Rybtke M T, Jakobsen T H, Hentzer M, Bjarnsholt T, Givskov M, Tolker-Nielsen T (2009) Antimicrob Agents Chemother 53:2432-2443
3. O'Loughlin C T, Miller L C, Siryaporn A, Drescher K, Semmelhack M F, Bassler B L (2013) Proc Natl Acad Sci USA 110:17981-17986
4. Hentzer M, Wu H, Andersen J B, Riedel K, Rasmussen T B, Bagge N, Kumar N, Schembri M A, Song Z, Kristoffersen P, Manefield M, Costerton J W, Molin S, Eberl L, Steinberg P, Kjelleberg S, Hoiby N, Givskov M (2003) EMBO J 22:3803-3815
5. Hentzer M, Riedel K, Rasmussen T B, Heydorn A, Andersen J B, Parsek M R, Rice S A, Eberl L, Molin S, Hoiby N, Kjelleberg S, Givskov M (2002) Microbiology 148:87-102
6. Rasmussen T B, Skindersoe M E, Bjarnsholt T, Phipps R K, Christensen K B, Jensen P O, Andersen J B, Koch B, Larsen T O, Hentzer M, Eberl L, Hoiby N, Givskov M (2005) Microbiology 151:1325-1340
7. Jakobsen T H, van G M, Phipps R K, Shanmugham M S, Christensen L D, Alhede M, Skindersoe M E, Rasmussen T B, Friedrich K, Uthe F, Jensen P O, Moser C, Nielsen K F, Eberl L, Larsen T O, Tanner D, Hoiby N, Bjarnsholt T, Givskov M (2012) Antimicrob Agents Chemother 56:2314-2325
8. Hinsberger S, de Jong J C, Groh M, Haupenthal J, Hartmann R W (2014) Eur J Med Chem 76C:343-351
9. Storz M P, Brengel C, Weidel E, Hoffmann M, Hollemeyer K, Steinbach A, Muller R, Empting M, Hartmann R W (2013) ACS Chem Biol 8:2794-2801
10. Sahner J H, Brengel C, Storz M P, Groh M, Plaza A, Muller R, Hartmann R W (2013) J Med Chem 56:8656-8664
11. Weidel E, de Jong J C, Brengel C, Storz M P, Braunshausen A, Negri M, Plaza A, Steinbach A, Muller R, Hartmann R W (2013) J Med Chem 56:6146-6155
12. Calfee M W, Coleman J P, Pesci E C (2001) Proc Natl Acad Sci USA 98:11633-11637
13. Pistorius D, Ullrich A, Lucas S, Hartmann R W, Kazmaier U, Muller R (2011) Chembiochem 12:850-853
14. Lesic B, Lepine F, Deziel E, Zhang J, Zhang Q, Padfield K, Castonguay M H, Milot S, Stachel S, Tzika A A, Tompkins R G, Rahme L G (2007) PLoS Pathog 3:1229-1239

15. Storz M P, Maurer C K, Zimmer C, Wagner N, Brengel C, de Jong J C, Lucas S, Musken M, Haussler S, Steinbach A, Hartmann R W (2012) J Am Chem Soc 134: 16143-16146
16. Coleman J P, Hudson L L, McKnight S L, Farrow J M, III, Calfee M W, Lindsey C A, Pesci E C (2008) J Bacteriol 190:1247-1255
17. Klein T, Henn C, de Jong J C, Zimmer C, Kirsch B, Maurer C K, Pistorius D, Muller R, Steinbach A, Hartmann R W (2012) ACS Chem Biol 7:1496-1501
18. Zender M, Klein T, Henn C, Kirsch B, Maurer C K, Kail D, Ritter C, Dolezal O, Steinbach A, Hartmann R W (2013) J Med Chem 56:6761-6774
19. Lu C, Kirsch B, Zimmer C, de Jong J C, Henn C, Maurer C K, Musken M, Haussler S, Steinbach A, Hartmann R W (2012) Chem Biol 19:381-390
20. Lu C, Maurer C K, Kirsch B, Steinbach A, Hartmann R W (2013) Angew Chem Int Ed Engl
21. Ilangovan A, Fletcher M, Rampioni G, Pustelny C, Rumbaugh K, Heeb S, Camara M, Truman A, Chhabra S R, Emsley J, Williams P (2013) PLoS Pathog 9:e1003508
22. Maurer C K, Steinbach A, Hartmann R W (2013) J Pharm Biomed Anal 86C:127-134
23. Zhang Y, Miller R M (1992) Appl Environ Microbiol 58:3276-3282
24. Essar D W, Eberly L, Hadero A, Crawford I P (1990) J Bacteriol 172:884-900
25. Musken M, Di F S, Dotsch A, Fischer R, Haussler S (2010) Microbiology 156:431-441
26. Musken M, Di F S, Romling U, Haussler S (2010) Nat Protoc 5:1460-1469
27. Mueller L N, de Brouwer J F, Almeida J S, Stal L J, Xavier J B (2006) BMC Ecol 6:1

The features of the present invention disclosed in the specification, the claims and/or the drawings may both separately and in any combination thereof be material for realizing the invention in various forms thereof.

The invention claimed is:

1. A compound of the following formula:

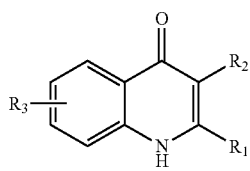
(A)

or a pharmacologically acceptable salt thereof, wherein
$R^1$ is a $C_6$- or $C_7$ alkyl group, in which one or two non-adjacent $CH_2$ group(s) may be replaced by O;
$R^2$ represents $(C_{1-3}$ alkyl)OH; $(C_{1-3}$ alkyl)O$(C_{1-3}$ alkyl); —C(=O)O(CH$_2$)CH$_3$; or —C(=O)NHOH;
$R^3$ represents H, halogen atom, CN, CF$_3$, NO$_2$, NH$_2$, —NHC(=O)R$^4$, —NHSO$_2$R$^4$, (CH$_2$)$_m$OR$^4$, SOCH$_3$, SOCN, SOCF$_3$, SO$_2$CH$_3$, SO$_2$CN, SO$_2$CF$_3$, SO$_2$NR$^5$R$^6$, C(=O)OC$_{1-6}$ alkyl, C(=O)NR$^5$R$^6$, COCH$_3$, COCF$_3$, or C(CN)$_3$;
$R^4$ in each case, independently of one another, represents a hydrogen atom; an alkyl; alkenyl; alkynyl; heteroalkyl; cycloalkyl; heterocycloalkyl; aryl; heteroaryl; aralkyl; or heteroaralkyl group;
$R^5$ and $R^6$ each independently represents a hydrogen atom; a methyl, an ethyl or an isopropyl group; or $R^5$ and $R^6$ are taken together to form a 5- to 8-membered saturated, unsaturated or aromatic heterocycle containing 1 to 4 N atoms or 1 to 3 heteroatoms selected from the group consisting of nitrogen, oxygen and sulphur, which heterocycle may be unsubstituted or mono-, di or trisubstituted by a halogen atom or R; or $R^5$ and $R^6$ are taken together to form a 5- to 8-membered saturated, unsaturated or aromatic heterocycle containing 1 to 3 heteroatoms selected from the group consisting of nitrogen, oxygen and sulphur, which is fused to one or two rings selected from the group consisting of cycloalkyl; heterocycloalkyl; alkylcycloalkyl; heteroalkylcycloalkyl; aryl; heteroaryl; aralkyl; and heteroaralkyl;

R represents H; —(CH$_2$)$_p$-L; —(CH$_2$)$_p$—OL; a $C_{1-6}$ heteroalkyl; a cycloalkyl; a heterocycloalkyl; an alkylcycloalkyl; a heteroalkylcycloalkyl; an aryl; a heteroaryl; an aralkyl; or a heteroaralkyl group; and m represents an integer from 1 to 6.

2. The compound according to claim 1, or a pharmacologically acceptable salt thereof, wherein the compound is represented by the following formula (B):

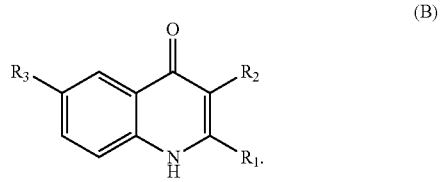
(B)

3. The compound according to claim 1, or a pharmacologically acceptable salt thereof, wherein $R^1$ is —(CH$_2$)$_6$CH$_3$; —(CH$_2$)$_4$O(CH$_2$)CH$_3$; or —(CH$_2$)O(CH$_2$)$_4$CH$_3$.

4. The compound according to claim 1, or a pharmacologically acceptable salt thereof, wherein the compound is selected from the group consisting of:

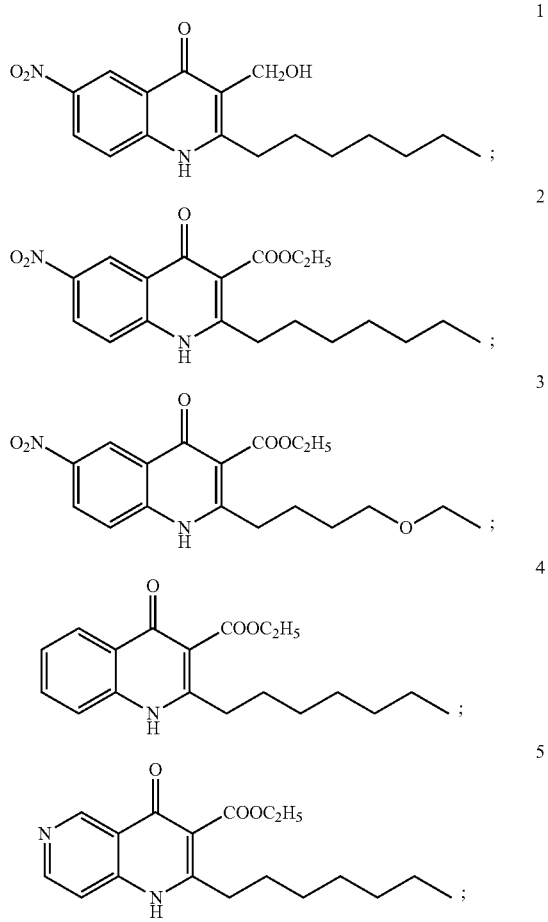

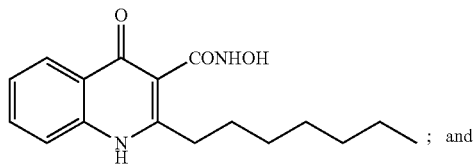

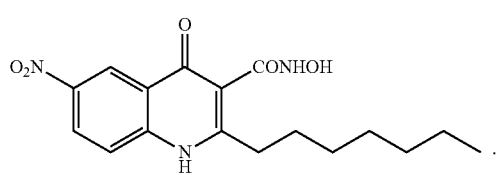

5. A pharmaceutical composition that comprises one or more compound(s) according to claim 1 and, optionally, at least one carrier substance, excipient and/or adjuvant.

6. A combination preparation containing at least one compound according to claim 1 and at least one further active pharmaceutical ingredient.

7. The combination preparation of claim 6, wherein the further active pharmaceutical ingredient is another antibiotic.

8. A coating for medicinal devices containing at least one compound according to claim 1.

9. A method of treating a subject suffering from *Pseudomonas aeruginosa* infection or *Burkholderia* infection, comprising administering to the subject an effective amount of a compound of claim 1.

* * * * *